United States Patent
Ferry et al.

(10) Patent No.: US 7,276,044 B2
(45) Date of Patent: Oct. 2, 2007

(54) SYSTEM AND METHODS FOR ADVANCING A CATHETER

(75) Inventors: Steven J. Ferry, Excelsior, MN (US); Jennifer R. Finney, St. Louis, MO (US); Cam Habeger, Big Lake, MN (US); Vincent Hackenmueller, Monticello, MN (US); Andrew F. Hall, St. Charles, MO (US); Reed A. Houge, Buffalo, MN (US); Scott G. Klimek, Spring Lake Park, MN (US); Michael J. Pikus, Golden Valley, MN (US)

(73) Assignee: Stereotaxis, Inc., St. Louis, MO (US)

( * ) Notice: Subject to any disclaimer, the term of this patent is extended or adjusted under 35 U.S.C. 154(b) by 452 days.

(21) Appl. No.: 10/138,710

(22) Filed: May 3, 2002

(65) Prior Publication Data

US 2002/0177789 A1    Nov. 28, 2002

Related U.S. Application Data

(60) Provisional application No. 60/288,879, filed on May 6, 2001.

(51) Int. Cl.
  *A61M 31/00* (2006.01)
  *A61M 37/00* (2006.01)
  *A61F 11/00* (2006.01)
(52) U.S. Cl. .................... 604/95.01; 606/108
(58) Field of Classification Search ........ 600/433–435, 600/585; 606/1, 108; 604/164.13, 165.01, 604/165.02, 166.04, 177, 178, 103.04, 523, 604/528, 533, 539, 95.01
See application file for complete search history.

(56) References Cited

U.S. PATENT DOCUMENTS

| | | | |
|---|---|---|---|
| 3,835,854 A | 9/1974 | Jewett | |
| 3,838,688 A | 10/1974 | May et al. | |
| 4,401,433 A | 8/1983 | Luther | |
| 4,564,014 A | 1/1986 | Fogarty et al. | |
| 4,753,248 A | 6/1988 | Engler et al. | |
| 4,795,434 A | 1/1989 | Kujawski | |
| 4,856,354 A | 8/1989 | Overbay | |
| 5,256,150 A | 10/1993 | Quiachon et al. | |
| 5,312,361 A | 5/1994 | Zadini et al. | |
| 5,346,498 A | 9/1994 | Greelis et al. | |
| 5,361,768 A | 11/1994 | Webler et al. | |
| 5,389,100 A | 2/1995 | Bacich et al. | |
| 5,485,846 A | 1/1996 | Webler et al. | |

(Continued)

FOREIGN PATENT DOCUMENTS

WO    WO 98/51364    5/1998

OTHER PUBLICATIONS

Merriam-Webster's Collegiate Dictionary, 10th ed. Merriam-Webster, Incorporated. p. 1101.*

*Primary Examiner*—Max F. Hindenburg
*Assistant Examiner*—Jonathan Foreman
(74) *Attorney, Agent, or Firm*—Harness, Dickey & Pierce, P.L.C.

(57) ABSTRACT

An advancer system is described for moving an elongate medical device within a body. The system includes a drive unit having a motor. The drive unit is configured to translate movement of the motor to the device so as to alternately advance and retract the device relative to the body. The advancer system also includes a user-operable control system configured to control the drive unit. The control system can interface with a magnetic navigation system. The above-described system allows an operating physician to control catheter advancement and retraction while remaining outside an x-ray imaging field. Thus the physician is freed from repeated x-ray exposure.

2 Claims, 23 Drawing Sheets

U.S. PATENT DOCUMENTS

| | | | |
|---|---|---|---|
| 5,486,161 A | 1/1996 | Lax et al. | |
| 5,531,713 A | 7/1996 | Mastronardi et al. | |
| 5,586,968 A | 12/1996 | Grundl et al. | |
| 5,592,942 A | 1/1997 | Webler et al. | |
| 5,654,864 A | 8/1997 | Ritter et al. | |
| 5,690,645 A | 11/1997 | Van Erp | |
| 5,759,153 A | 6/1998 | Webler et al. | |
| 5,779,623 A * | 7/1998 | Bonnell | 600/114 |
| 5,810,835 A | 9/1998 | Ryan et al. | |
| 5,827,313 A | 10/1998 | Ream | |
| 5,931,818 A | 8/1999 | Werp et al. | |
| 5,957,941 A | 9/1999 | Ream | |
| 6,004,271 A | 12/1999 | Moore | |
| 6,013,030 A | 1/2000 | Webler et al. | |
| 6,014,580 A | 1/2000 | Blume et al. | |
| 6,015,414 A | 1/2000 | Werp et al. | |
| 6,128,174 A | 10/2000 | Ritter et al. | |
| 6,148,823 A | 11/2000 | Hastings | |
| 6,152,933 A | 11/2000 | Werp et al. | |
| 6,157,853 A | 12/2000 | Blume et al. | |
| 6,171,234 B1 * | 1/2001 | White et al. | 600/102 |
| 6,193,736 B1 | 2/2001 | Webler et al. | |
| 6,212,419 B1 | 4/2001 | Blume et al. | |
| 6,241,671 B1 | 6/2001 | Ritter et al. | |
| 6,292,678 B1 | 9/2001 | Hall et al. | |
| 6,296,604 B1 | 10/2001 | Garibaldi et al. | |
| 6,298,257 B1 | 10/2001 | Hall et al. | |
| 6,304,768 B1 | 10/2001 | Blume et al. | |
| 6,315,709 B1 | 11/2001 | Garibaldi et al. | |
| 6,319,227 B1 | 11/2001 | Mansouri-Ruiz | |
| 6,330,467 B1 | 12/2001 | Creighton, IV et al. | |
| 6,352,363 B1 | 3/2002 | Munger et al. | |
| 6,358,199 B1 | 3/2002 | Pauker et al. | |
| 6,364,823 B1 | 4/2002 | Garibaldi et al. | |
| 6,375,606 B1 | 4/2002 | Garibaldi et al. | |
| 6,385,472 B1 | 5/2002 | Hall et al. | |
| 6,401,723 B1 | 6/2002 | Garibaldi et al. | |
| 6,409,672 B2 | 6/2002 | Webler et al. | |
| 6,428,551 B1 | 8/2002 | Hall et al. | |
| 6,459,924 B1 | 10/2002 | Creighton, IV et al. | |
| 6,475,223 B1 * | 11/2002 | Werp et al. | 606/108 |
| 6,505,062 B1 | 1/2003 | Ritter et al. | |
| 6,507,751 B2 | 1/2003 | Blume et al. | |
| 6,522,909 B1 | 2/2003 | Garibaldi et al. | |
| 6,524,303 B1 | 2/2003 | Garibaldi | |
| 6,527,782 B2 | 3/2003 | Hogg et al. | |
| 6,537,196 B1 | 3/2003 | Creighton, IV et al. | |
| 6,542,766 B2 | 4/2003 | Hall et al. | |
| 6,562,019 B1 | 5/2003 | Sell | |
| 6,623,433 B2 | 9/2003 | Webler et al. | |
| 6,630,879 B1 | 10/2003 | Creighton, IV et al. | |
| 6,662,034 B2 | 12/2003 | Segner et al. | |
| 6,677,752 B1 | 1/2004 | Creighton, IV et al. | |
| 6,702,804 B1 | 3/2004 | Ritter et al. | |
| 6,726,675 B1 * | 4/2004 | Beyar | 604/510 |
| 6,733,511 B2 | 5/2004 | Hall et al. | |
| 6,755,816 B2 | 6/2004 | Ritter et al. | |
| 6,817,364 B2 | 11/2004 | Garibaldi et al. | |
| 6,834,201 B2 | 12/2004 | Gillies et al. | |
| 6,902,528 B1 | 6/2005 | Garibaldi et al. | |
| 6,911,026 B1 | 6/2005 | Hall et al. | |
| 6,968,846 B2 | 11/2005 | Viswanathan | |
| 6,975,197 B2 | 12/2005 | Creighton, IV | |
| 6,980,843 B2 | 12/2005 | Eng et al. | |
| 7,008,418 B2 | 3/2006 | Hall et al. | |
| 7,010,338 B2 | 3/2006 | Ritter et al. | |
| 7,019,610 B2 | 3/2006 | Creighton, IV et al. | |
| 7,020,512 B2 | 3/2006 | Ritter et al. | |
| 7,066,924 B1 | 6/2006 | Garibaldi et al. | |
| 2001/0038683 A1 | 11/2001 | Ritter et al. | |
| 2002/0019644 A1 | 2/2002 | Hastings et al. | |
| 2004/0006301 A1 | 1/2004 | Sell, et al. | |
| 2004/0019447 A1 | 1/2004 | Shachar | |
| 2004/0064153 A1 | 4/2004 | Creighton, IV et al. | |
| 2004/0068173 A1 | 4/2004 | Viswanathan | |
| 2004/0096511 A1 | 5/2004 | Harburn et al. | |
| 2004/0133130 A1 | 7/2004 | Ferry et al. | |
| 2004/0157082 A1 | 8/2004 | Ritter et al. | |
| 2004/0158972 A1 | 8/2004 | Creighton, IV et al. | |
| 2004/0186376 A1 | 9/2004 | Hogg et al. | |
| 2004/0199074 A1 | 10/2004 | Ritter et al. | |
| 2004/0249262 A1 | 12/2004 | Werp et al. | |
| 2004/0249263 A1 | 12/2004 | Creighton, IV | |
| 2004/0260172 A1 | 12/2004 | Ritter et al. | |
| 2005/0020911 A1 | 1/2005 | Viswanathan et al. | |
| 2005/0043611 A1 | 2/2005 | Sabo et al. | |
| 2005/0065435 A1 | 3/2005 | Rauch et al. | |
| 2005/0096589 A1 | 5/2005 | Shachar | |
| 2005/0113628 A1 | 5/2005 | Creighton, IV et al. | |
| 2005/0113812 A1 | 5/2005 | Viswanathan et al. | |
| 2005/0119687 A1 | 6/2005 | Dacey, Jr. et al. | |
| 2005/0182315 A1 | 8/2005 | Ritter et al. | |
| 2005/0256398 A1 | 11/2005 | Hastings, et al. | |
| 2006/0009735 A1 | 1/2006 | Viswanathan et al. | |
| 2006/0025679 A1 | 2/2006 | Viswanathan et al. | |
| 2006/0036125 A1 | 2/2006 | Viswanathan et al. | |
| 2006/0036163 A1 | 2/2006 | Viswanathan | |
| 2006/0041178 A1 | 2/2006 | Viswanathan et al. | |
| 2006/0041179 A1 | 2/2006 | Viswanathan et al. | |
| 2006/0041180 A1 | 2/2006 | Viswanathan et al. | |
| 2006/0041181 A1 | 2/2006 | Viswanathan et al. | |
| 2006/0041245 A1 | 2/2006 | Ferry et al. | |
| 2006/0058646 A1 | 3/2006 | Viswanathan | |
| 2006/0074297 A1 | 4/2006 | Viswanathan | |
| 2006/0079745 A1 | 4/2006 | Viswanathan | |
| 2006/0079812 A1 | 4/2006 | Viswanathan | |
| 2006/0093193 A1 | 5/2006 | Viswanathan | |
| 2006/0094956 A1 | 5/2006 | Viswanathan | |
| 2006/0100505 A1 | 5/2006 | Viswanathan | |
| 2006/0114088 A1 | 6/2006 | Shachar | |
| 2006/0116633 A1 | 6/2006 | Shachar | |
| 2006/0144407 A1 | 7/2006 | Aliberto et al. | |
| 2006/0144408 A1 | 7/2006 | Ferry | |

\* cited by examiner

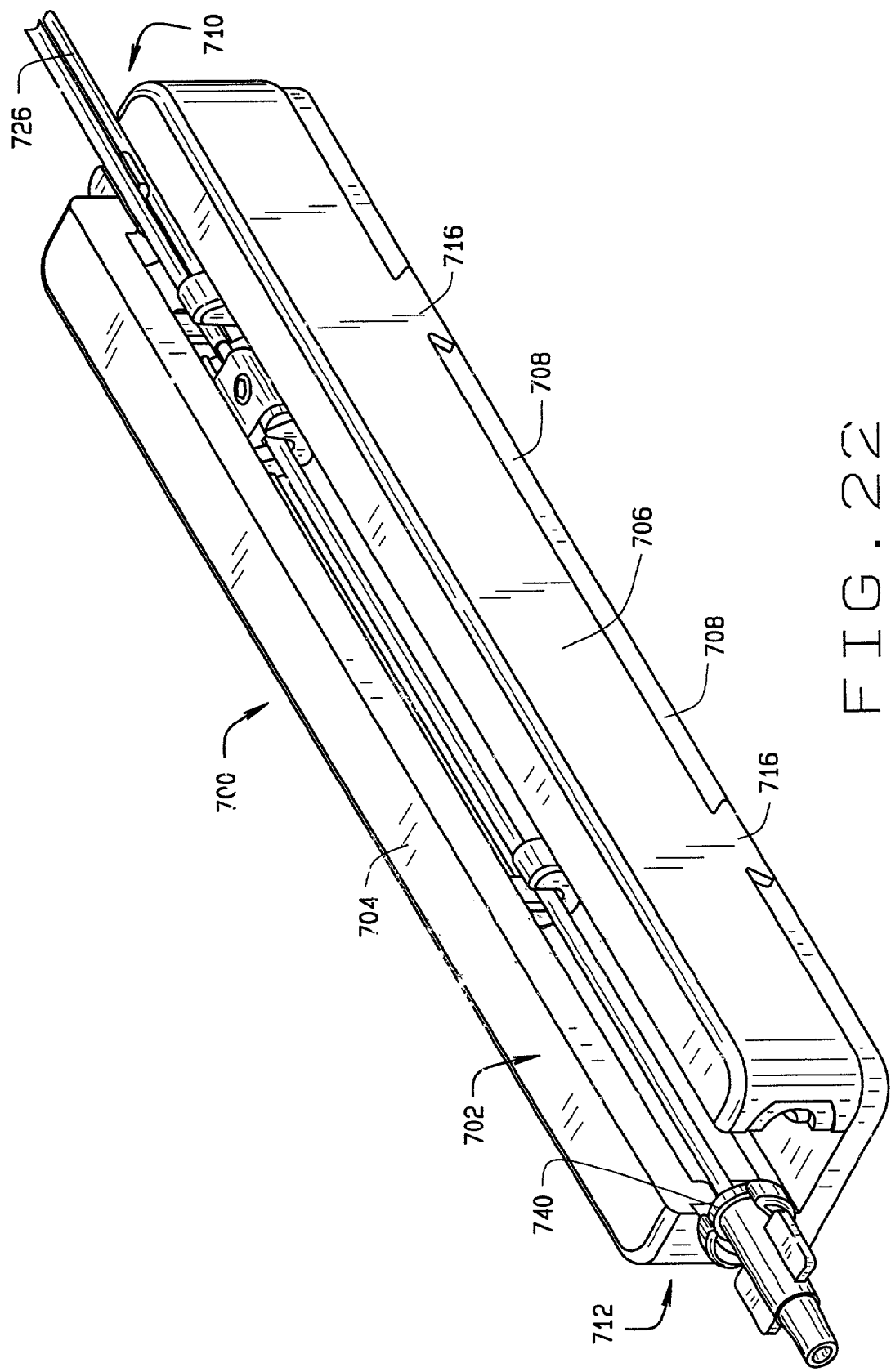

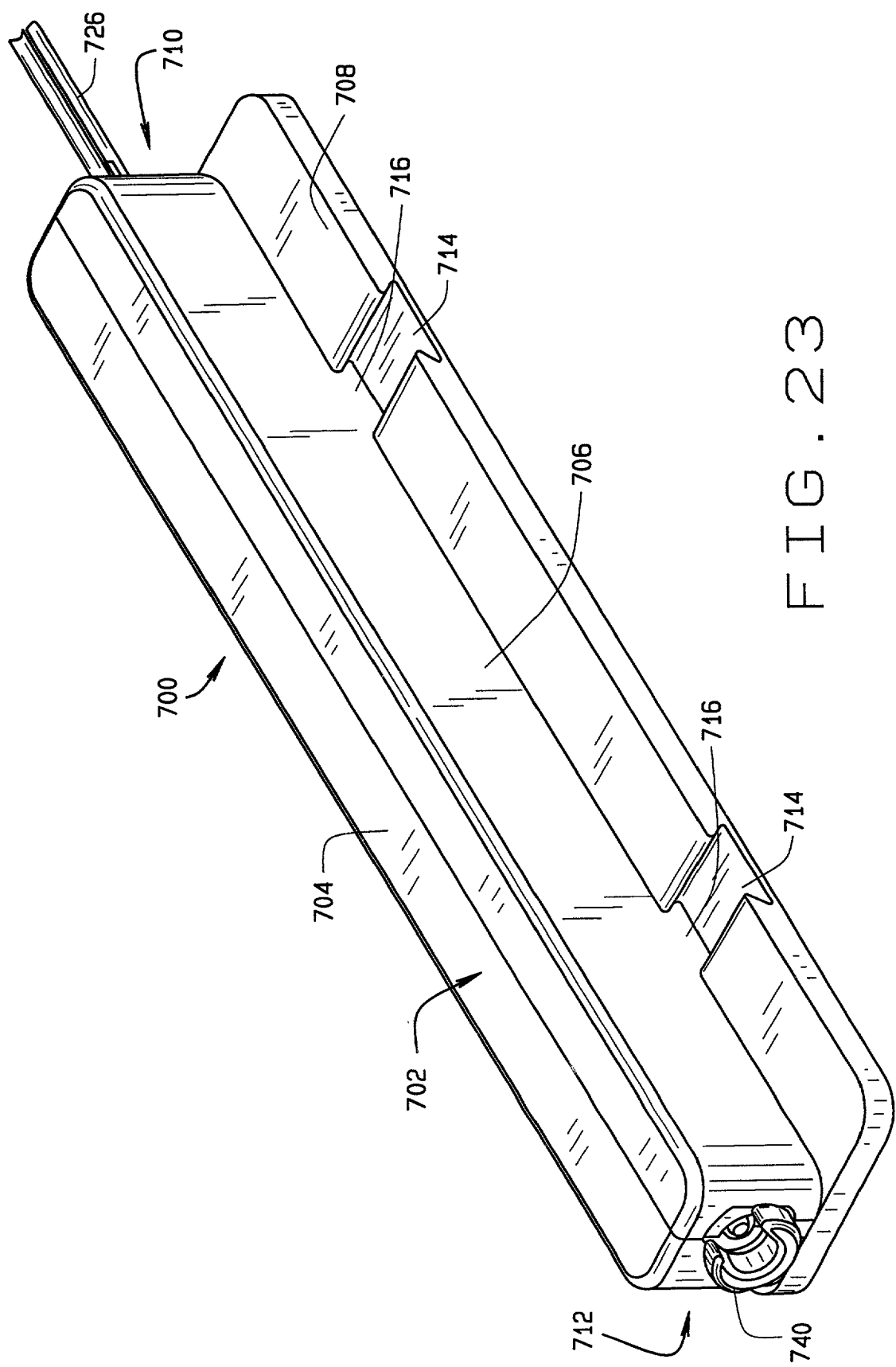

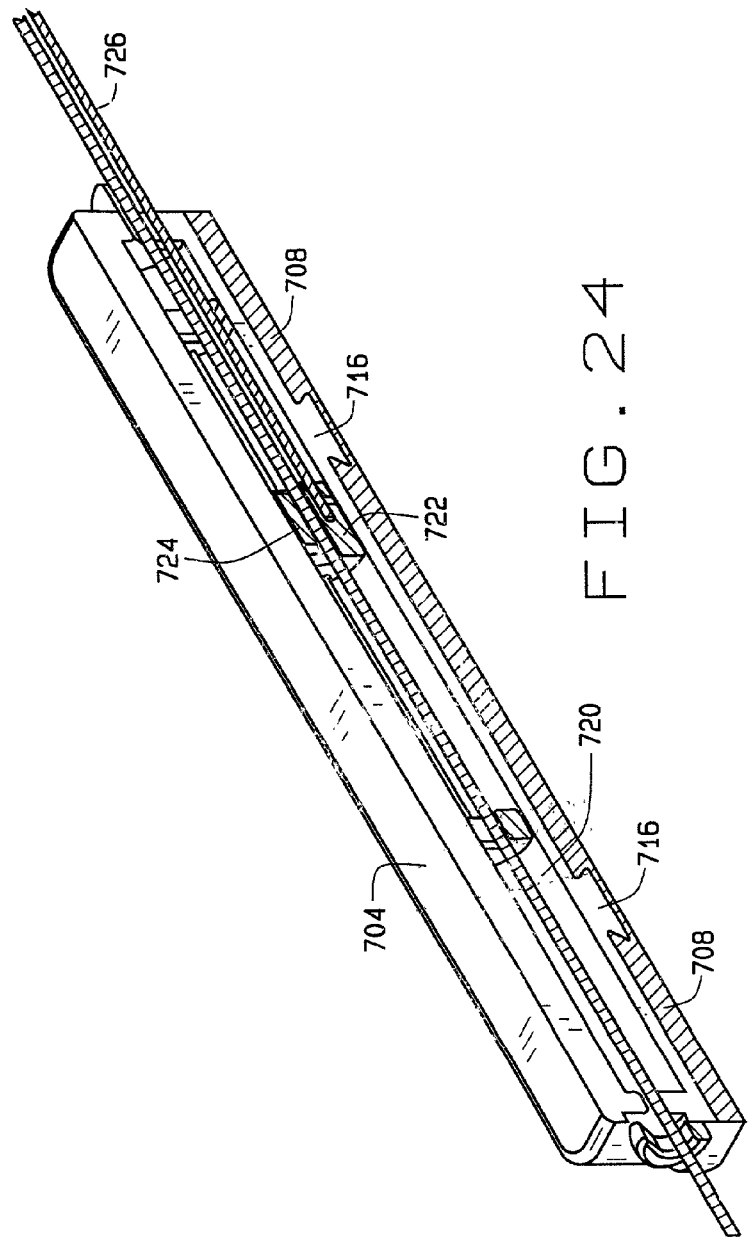
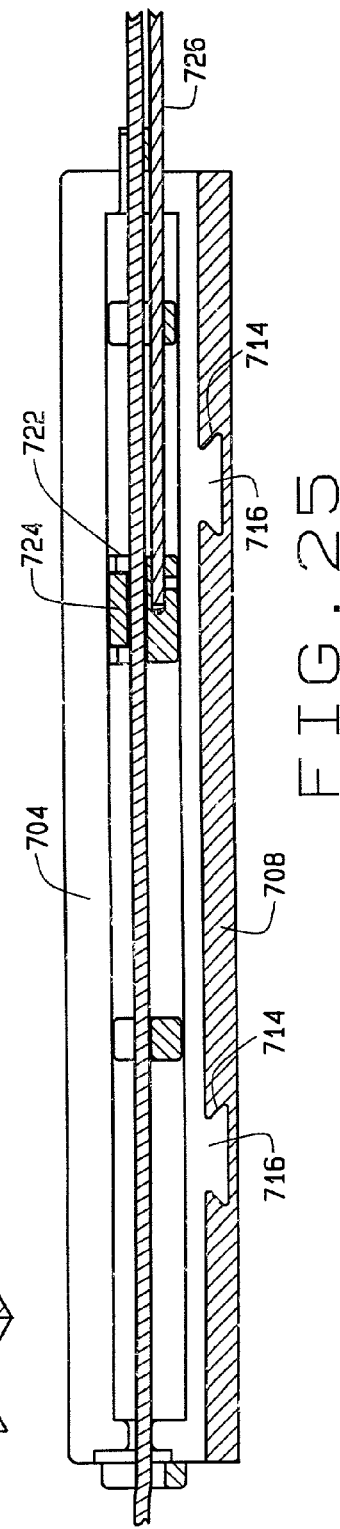

SYSTEM AND METHODS FOR ADVANCING A CATHETER

CROSS-REFERENCE TO RELATED APPLICATION

This application claims priority of prior provisional application Ser. No. 60/288,879, filed May 6, 2001, entitled System and Methods for Advancing a Catheter.

FIELD OF THE INVENTION

The present invention relates generally to systems and methods of advancing medical devices in the body, and in particular, to advancing catheters during magnetic navigation.

BACKGROUND OF THE INVENTION

Physicians currently utilize a variety of techniques to control elongate surgical tools and devices such as catheters. As a catheter, endoscope, or other medical device is advanced ever deeper into tortuous confines of a patient's vasculature, the device becomes correspondingly more difficult to control. Although real-time x-ray imaging can provide guidance to an operating physician during such a procedure, over time the physician runs the risk of repeatedly being exposed to x-ray fields if he or she remains in the vicinity of the patient while x-rays are being projected.

In many applications, magnetic fields can be used to steer the tip of a catheter or other surgical tool. Magnetic steering techniques provide precise, computer-assisted control of a catheter tip and allow an operating physician to remain outside the x-ray imaging field while steering a catheter tip. Nevertheless, during some medical procedures such as cardiac mapping, the physician may find it preferable to advance or retract the catheter by mechanical means. During cardiac mapping, a catheter is repeatedly advanced and retracted within a patient's heart while a tip of the catheter is redirected to different locations on the heart wall.

Although systems have been developed that would automatically advance and/or retract elongate medical devices, the object of such systems has been to provide the capability for retracting, rather than advancing, a medical device within a patient. For example, systems are in use that collect imaging information generated by a rotating imaging device as the device is retracted from the vasculature of a patient. If such a system were to be used to advance a medical device in a patient during a medical procedure, perforation and injury to the patient could result, particularly when the medical device has a stiff distal tip. A physician might choose to use an automatic retractor in order to reduce time and fatigue during a medical procedure. However, when the physician must be present in the operating field to manually control advancement of a device, the physician still faces repeated x-ray exposure. Thus it would be desirable to provide a way for physicians to mechanically advance and retract medical devices while outside the x-ray field.

SUMMARY OF THE INVENTION

The present invention relates to systems and methods for automatically advancing medical devices. In one embodiment, the invention is directed to an advancer system for moving an elongate medical device within a body. The system comprises a drive unit having a motor. The drive unit is configured to translate movement of the motor to the device so as to alternately advance and retract the device relative to the body. The advancer system also includes a user-operable control system configured to control the drive unit.

The above-described system allows an operating physician to control advancement and retraction of a medical device while remaining outside the x-ray field. Thus the physician is freed from manually advancing and retracting medical devices, and can even work remotely from the surgical site to reduce repeated x-ray exposure. Embodiments of the present invention are particularly useful in combination with a magnetic navigation system to advance and retract magnetically steerable medical devices.

BRIEF DESCRIPTION OF THE DRAWINGS

FIG. 22 is a perspective view of a slide unit constructed according to a seventh embodiment of the present invention, with the slide unit open;

FIG. 23 is a perspective view of the slide unit shown in FIG. 22, with the advancer closed;

FIG. 24 is a perspective view of the left half of the housing of the slide unit shown in FIG. 22;

FIG. 25 is a front elevation view of the left half of the housing of the slide unit shown in FIG. 22;

DETAILED DESCRIPTION OF THE INVENTION

Figure 1:
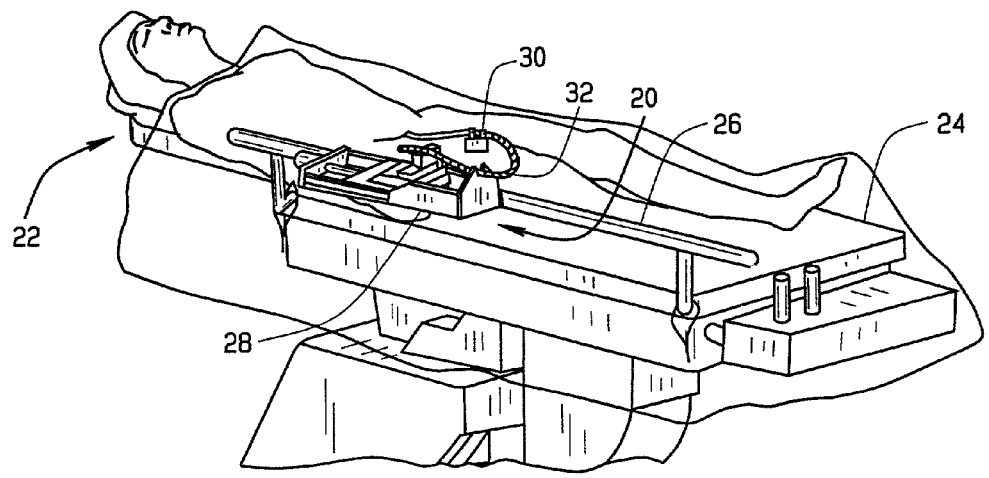
FIG. 1 is a perspective view of a patent on a bed, showing a drive unit, control cable and slide unit of a first embodiment of an advancer system of the present invention, in position to advance a catheter in a patient's femoral artery.

A first embodiment of an advancer system, or advancer, constructed according to the principles of this invention is indicated generally as 20 in FIG. 1. The advancer 20 comprises a drive unit 28 that is connected to a slide unit 30 via a control cable 32. The advancer drive unit 28 is shown as it would be mounted on a patient table 22 for moving an elongate medical device in a patient lying on the table. The table 22 has a support surface 24 and one or two side rails 26. The medical device might be, for example, a catheter that is being advanced through the patient's vasculature, during a cardiac mapping procedure. The slide unit 30 is shown resting on a leg of the patient. The advancer system 20 also includes a control system having a controller or processor, and at least one operator input device, described in more detail below.

Figure 2:
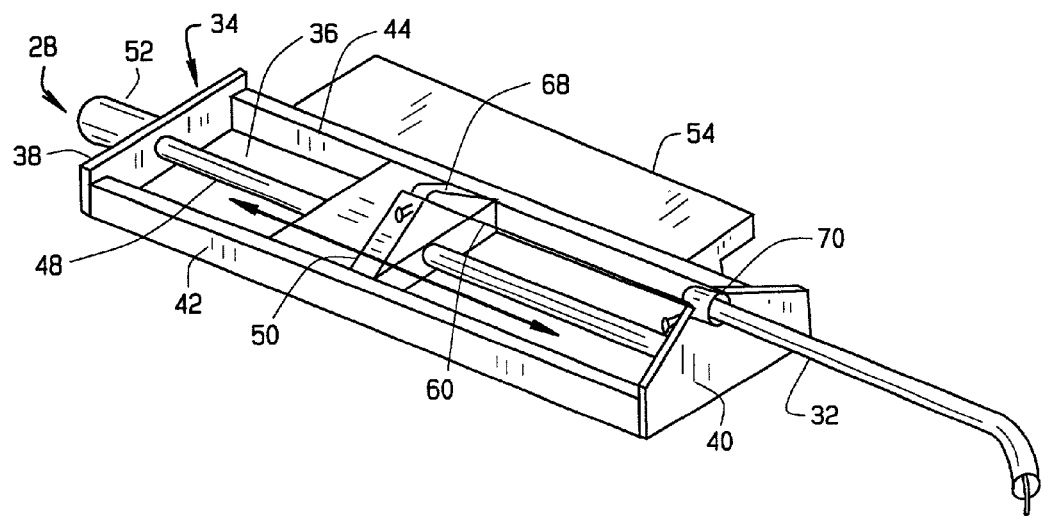
FIG. 2 is a perspective view of the drive unit shown in FIG. 1.

As shown in FIG. 2, the drive unit 28 comprises a frame 34 having a bottom 36, first and second ends 38 and 40, and first and second sides 42 and 44. A cover (not shown) may also be provided to enclose the drive unit. A lead screw 48 extends longitudinally through the frame 34, between the first and second ends 38 and 40. A carrier 50 is threadedly mounted on the lead screw 48. The lead screw 48 is driven by an electric motor 52 mounted on the first end 38 of the frame 34, such that rotation of the lead screw causes the carrier 50 to move within the frame 34. The drive unit 28 includes a clip 54 for securing the drive unit to the patient table, for example, to side rail 26.

Figure 3:
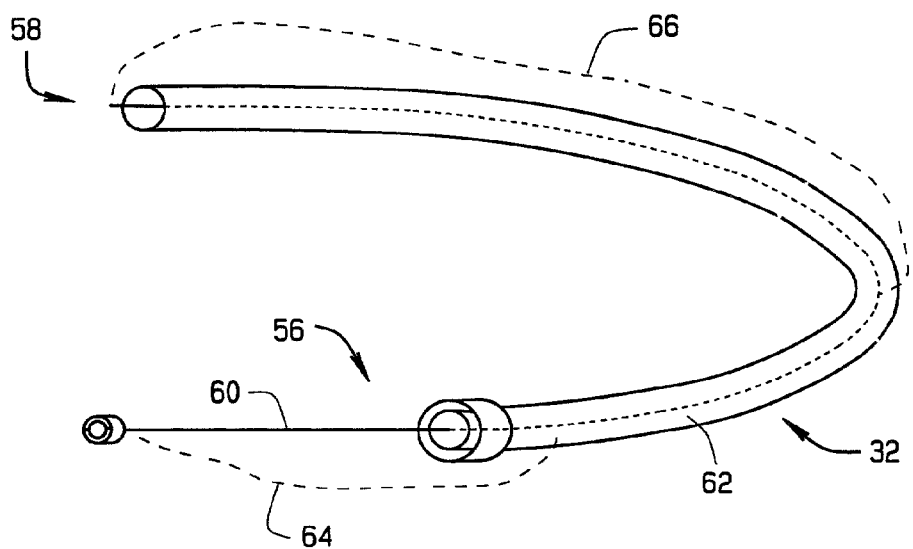
FIG. 3 is an illustration of the control cable shown in FIG. 1.

As shown in FIG. 3, the control cable 32 has a proximal end 56 and a distal end 58. The control cable 32 comprises a wire 60 enclosed in an outer sheath 62. The proximal portion 64 of the wire 60 is preferably relatively stiff, while the distal portion 66 of the wire is preferably more flexible. The proximal end of the wire 60 is secured in a mounting 68 on the carrier 50, and the proximal end of the sheath 62 is secured in a mounting 70 (shown in FIG. 2) on the second end 40 of the frame 34. Thus movement of the carrier 50 in the frame 34 moves the wire 60 relative to its sheath 62.

Figure 4:
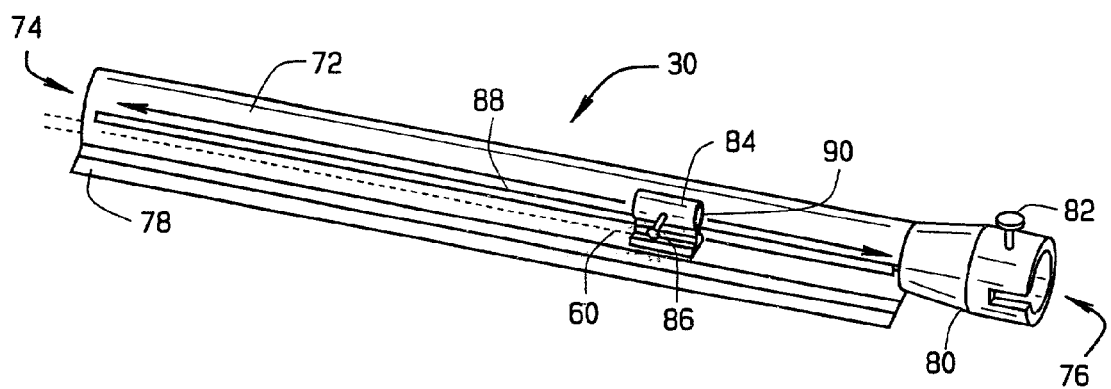
FIG. 4 is an illustration of the slide unit shown in FIG. 1.

As shown in FIG. 4, the slide unit 30 includes a tube 72 having proximal and distal ends 74 and 76. The tube 72 can be flexible so as to allow the tube to conform in shape to its supporting surface, e.g. a leg of the patient as shown in FIG. 1. An attachment flap 78 projects from the tube 72, for securing the slide unit 30. The distal end 76 has a socket 80 for receiving a sheath (not shown) to enclose the distal end portion of the medical device being advanced. The socket 80 includes a setscrew 82 for securing the sheath.

A slider 84 is slidably mounted in the tube 72. The slider 84 has a passage 90 therethrough for receiving an elongate medical device, such as a catheter, and a thumbscrew 86 for engaging a medical device in the passage. The tube 72 has a longitudinally extending slot 88 through which the thumbscrew 86 extends. The proximal end of the tube 72 connects to the distal end of the control cable 32, and the distal end of the wire 60 is attached to the slider 84. Thus, movement of the wire 60 moves the slider 84 within the tube 72.

Figure 5:
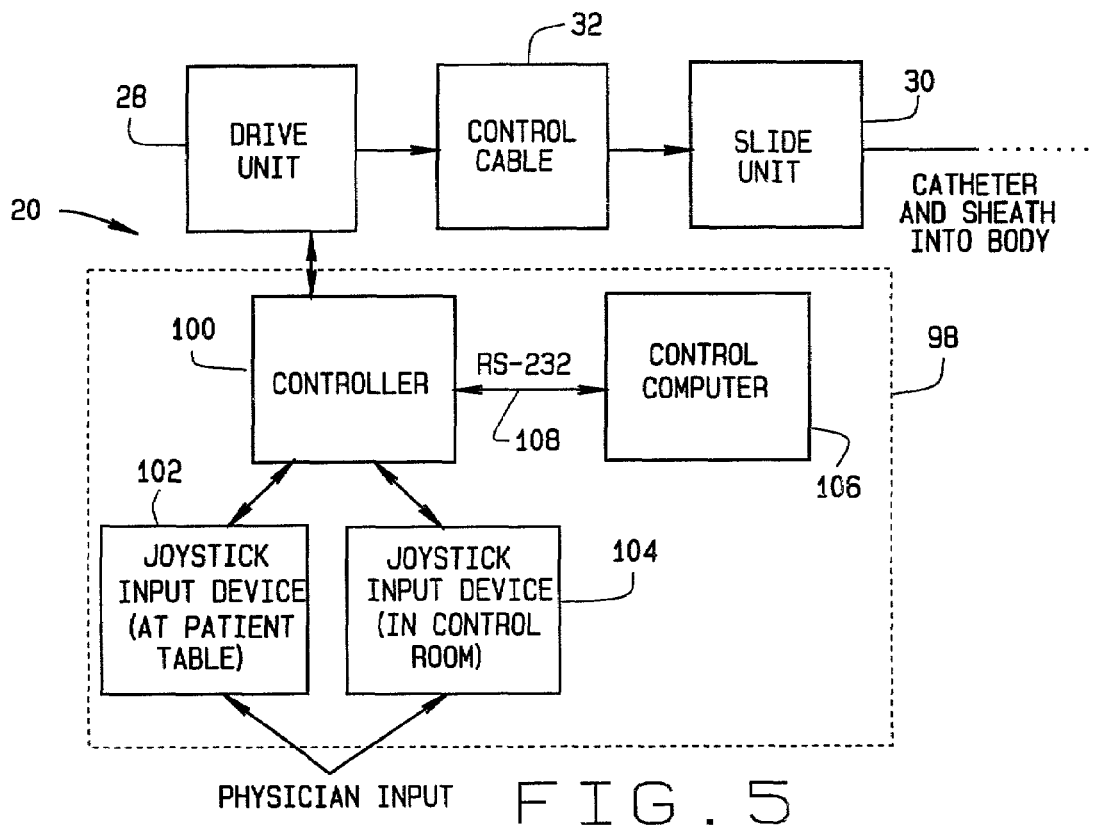
FIG. 5 is a block diagram of one embodiment of an advancer control system.

As shown in FIG. 5, the advancer system 20 also comprises a control system 98. The control system includes a processor or controller 100, configured to receive operator input from, for example, one or more joystick devices, such as a joystick device 102 located at the patient table 22, or a joystick device 104 located in a remote control room. The controller 100 interfaces with the drive unit 28, selectively operating the motor 52. The controller 100 also interfaces with a control computer 106, e.g. via an EIA RS-232 interface 108 or some other suitable interface. In one embodiment, the computer 106 is part of a magnetic navigation system (MNS) for controlling a magnet system for magnetically guiding a magnetically responsive medical device inside a patient's body. The operator joystick 102 or 104 allows the operator to input information about the orientation and advancement/retraction of the medical device. The computer 106 controls one or more magnets of the magnetic navigation system to apply a magnetic field to orient the medical device in a selected direction. The computer 106 also can control the motor 52, via the controller 100, to advance or retract the magnetic medical device.

In other embodiments, the controller 100 interfaces with the computer 106 for other purposes, e.g. to move the catheter based on physiological and/or imaging information. In yet another embodiment, the drive unit 28 is operated in a standalone manner, i.e. the controller 100 controls the drive unit 28 without interfacing with another computer such as computer 106.

Figure 6:
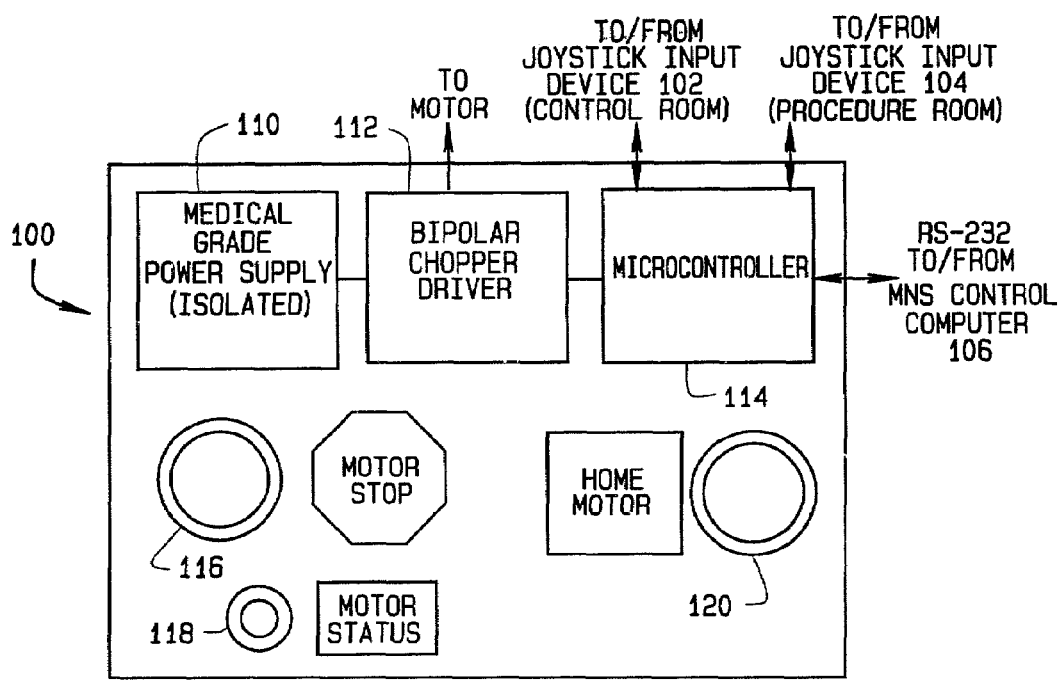
FIG. 6 is a schematic block diagram of the controller shown in FIG. 5.

As shown in FIG. 6, the controller 100 includes a power supply 110, which is preferably an isolated medical grade supply, for supplying power to a driver circuit 112 for driving the motor 52. In this first embodiment, the driver circuit 112 is a bipolar chopper driver circuit. The controller 100 also includes a microcontroller 114 that interfaces with the control computer 106, input devices 102 and/or 104, and the driver circuit 112. The microcontroller 114 may be controlled via software and/or hardware, and may be configured to provide the advancer 20 with additional capabilities not explicitly described herein but within the scope of the present invention.

The controller 100 also includes a "Motor Stop" button 116 for disconnecting the power supply 110 from the motor 52, e.g. in an emergency. The "Motor Stop" button 116 is hardwired to the power supply 110 for safety. The controller 100 may also include a "Motor Status" indicator 118, which might be, for example, a light emitting diode (LED) or other indicator to show when the advancer 20 is receiving power from the power supply 110. For example, the "Motor Status" indicator 118 is lighted green when the power supply 110 is delivering power and is lighted yellow when power delivery is below an expected level. In this first embodiment, the button 116 and the indicator 118 are located on the cover (not shown) of the drive unit 28. As further described below, the controller 100 may also include a "Motor Home" button 120 which also may be located on the cover (not shown) of the drive unit 28.

Figure 7:
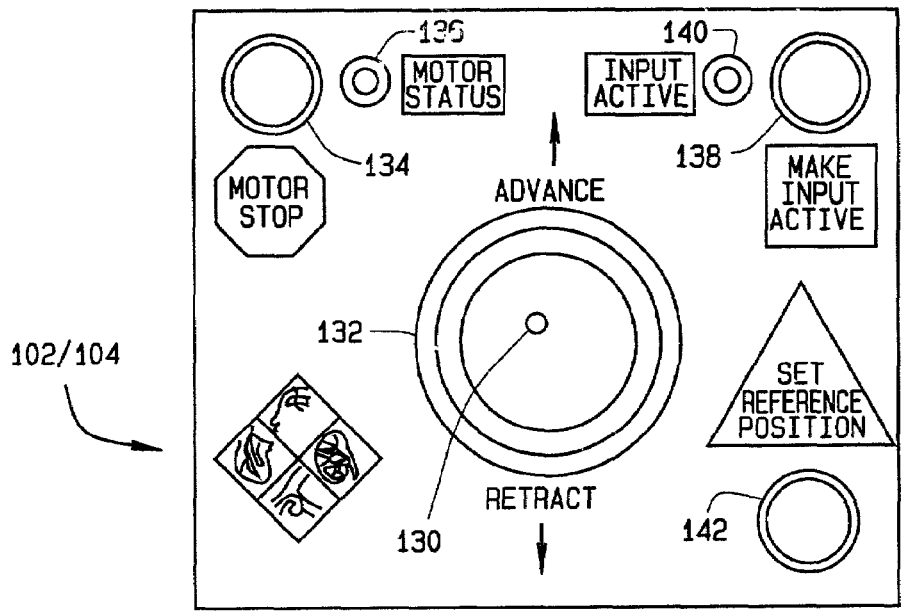
FIG. 7 is a schematic block diagram of a joystick input device shown in FIG. 5.

As shown in FIG. 7, the joystick devices 102 and/or 104 have a stick with a motion-enable button 130 which the operator manipulates to operate the advancer 20 to advance and retract the medical device. Of course, instead of a joystick, a foot pedal or other device can be provided to facilitate the operator's use of the advancer. The joystick devices preferably also include a "Motor Stop" button 134 and a "Motor Status" indicator 136 which function as described with respect to the "Motor Stop" button 116 and "Motor Status" indicator 118 (described above with respect to FIG. 6). As further described below, the joystick devices 102 and 104 include a "Make Input Active" button 138, an "Active Input" indicator 140, which may be, for example, an LED, and a "Set Reference Position" button 142.

In preparing the advancer 20 for use in a medical procedure, the slide unit 30 is placed upon a surface, for example the patient's leg. The flap 78 aids in fixing the slide unit in place. A hemostasis valve from the protective sheath of the catheter is attached to the socket 80 and secured with thumbscrew 82. The hemostasis valve does not move during use of the advancer 20, and instead the catheter or other medical device advances and retracts relative to the sheath. The motor drive unit 28 is preferably located outside of the sterile operating field so that it does not have to be sterilized and kept sterile, while the control cable 32 and slide unit 30 are located inside the sterile field, and are kept sterile. The slide unit 30 is attached to a sterile drape on the leg of the patient via the attachment flap 78 with towel clips (not shown), or other suitable fasteners, to prevent injury in case of patient movement.

The control cable 32 is attached to the slide unit 30 to translate motion of the motor 52 to the slider 84 of the slide unit 30. More specifically, and as shown in FIGS. 2 through 4, the distal end of the outer sheath 62 of the control cable 32 is attached to a connector (not shown) on the proximal end 74 of the tube 72, and the wire 60 is attached to the slider 84. An elongate medical device, such as a catheter, is then attached to the slider 84. For example, a 7-French-size mapping catheter manufactured by Stereotaxis, Inc., of St. Louis, Mo., is placed in the slider 84 and secured with thumbscrew 86. The slider 84 can be attached to the catheter at any point along the catheter, depending on a desired location in the heart of the patient to be reached by the catheter. By loosening the attachment of the slider 84 to the catheter, the catheter position can be adjusted during the procedure, for example, to allow for manual navigation of the catheter. After catheter adjustment, the slider 84 is reattached to the catheter. Alternatively, after the catheter is freed from the slider 84, the catheter can be quickly removed.

At the beginning of a procedure, the operator depresses the "Motor Home" button 120 to place the motor 52 in a starting position. More specifically, the motor 52 is reversed until a proximal limit switch (not shown) on the lead screw 48 is activated. A fully retracted starting position of the motor 52 then is registered with the microcontroller 114 control software. The operator selects a joystick device 102 or 104 as active by depressing the "Make Input Active" button 138 on the device. When a device 102 or 104 is selected as active, the controller 100 recognizes commands from the selected device 102 or 104 and ignores commands from any other input device(s) 102 and 104. The "Active Input" indicator 140 on the selected device 102 or 104 is lighted green to indicate the selection. If the controller 100 is in an automated mapping mode as further described below, the "Active Input" indicator 140 is lighted yellow on each input device 102, and depressing the "Make Input Active" button 138 on any device 102 or 104 has no effect on the advancer 20.

When the advancer 20 is in use, the operator enters input via a remotely located input device 104, or via an input device 102 at the table 22 as previously described. The operation of the joystick causes the motor 52 to operate, which in turn causes the lead screw 48 to turn, which causes the carrier 50 to translate in the frame 34. The translation of the carrier 50 moves the wire 60, which in turn moves the slider 84 within the tube 72. Motion of the slider 84 pushes and pulls the catheter secured in the slider 84. Because the motor 52 moves only when button 130 is depressed, unintentional motion is prevented if the joystick is accidentally bumped. The controller 100 signals the motor 52 to advance or reverse in accordance with the joystick input. The speed of the motor 52 is continuously variable and proportional to a distance of advancement or retraction of the joystick.

The control cable 32 translates motion of the motor 52 to the slider unit 30. More specifically, as the motor 52 turns, the wire 60 moves relative to the outer sheath 62. Thus the motion is translated through the control cable 32, and the slider 84 can be alternately advanced and retracted relative to the tube 72. The slide tube 72 supports the catheter to prevent it from buckling as the slider 84 is advanced and retracted. The relatively stiff proximal segment 64 resists buckling of the wire 60 during advancement when motion of the motor 52 is translated to the catheter. The flexible distal segment 66 allows the control cable 32 to bend readily and allows the slide unit 30 to lie flat on the leg of the patient. The flexible segment 66 also compensates for movement by the patient.

During operation, the operator can press the "Set Reference Position" button 142, to save a current position of the motor 52 (for example, in the microcontroller 114). The operator thus can use the saved motor 52 position as a reference point for navigation during a procedure. The current position of the motor 52 also is displayed with other status information for the motor 52 as described below.

The advancer 20 can be adapted for use in automated cardiac mapping, in which case the controller 100 receives commands from the MNS control computer 106 to navigate the catheter during cardiac mapping. The MNS computer 106 sends mapping commands to an active device 102 via controller 100, and "Active Input" LED 140 is lighted yellow on each input device 102 and 104.

Figure 8A:
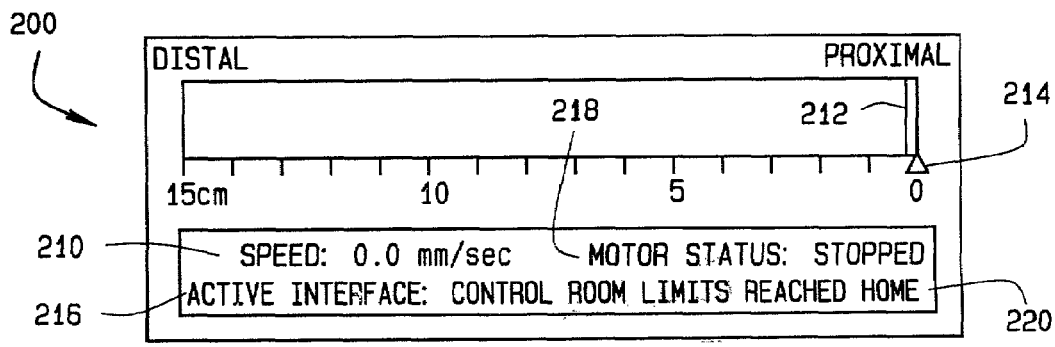
FIG. 8A is an illustration of a magnetic navigation system control computer display at the start of a procedure.
Figure 8B:
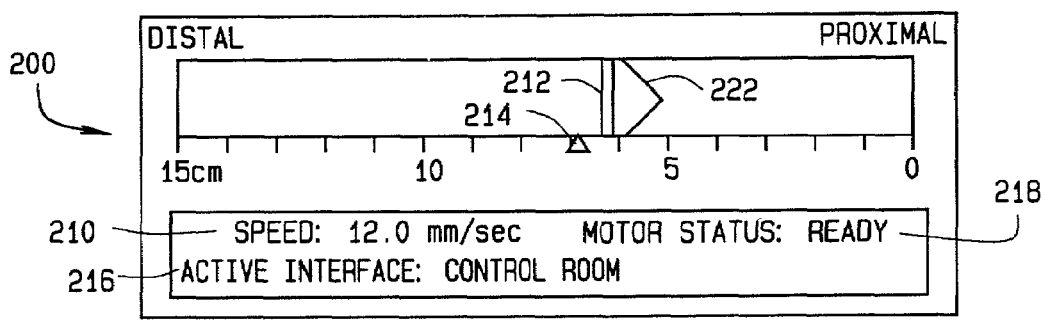
FIG. 8B is an illustration of a magnetic navigation system control computer display during a procedure.

The controller 100 also sends status information to the MNS control computer 106 for display as shown in FIGS. 8A and 8B. FIG. 8A illustrates an exemplary MNS control computer display 200 at the start of a procedure. The "Motor Home" button 120 (shown in FIG. 6) has been pressed to place the motor 52 in a starting position and the motor 52 is stopped. Information displayed includes a motor speed indicator 210 and a motor position indicator 212, a reference position indicator 214, an active input device indicator 216, a motor status indicator 218, and a limits-reached indicator 220. FIG. 8B illustrates an exemplary display 200 during a procedure. The reference position indicator 214 indicates that a reference position is set, and a direction indicator 222 indicates that the advancer 20 is retracting the catheter.

Figure 9:
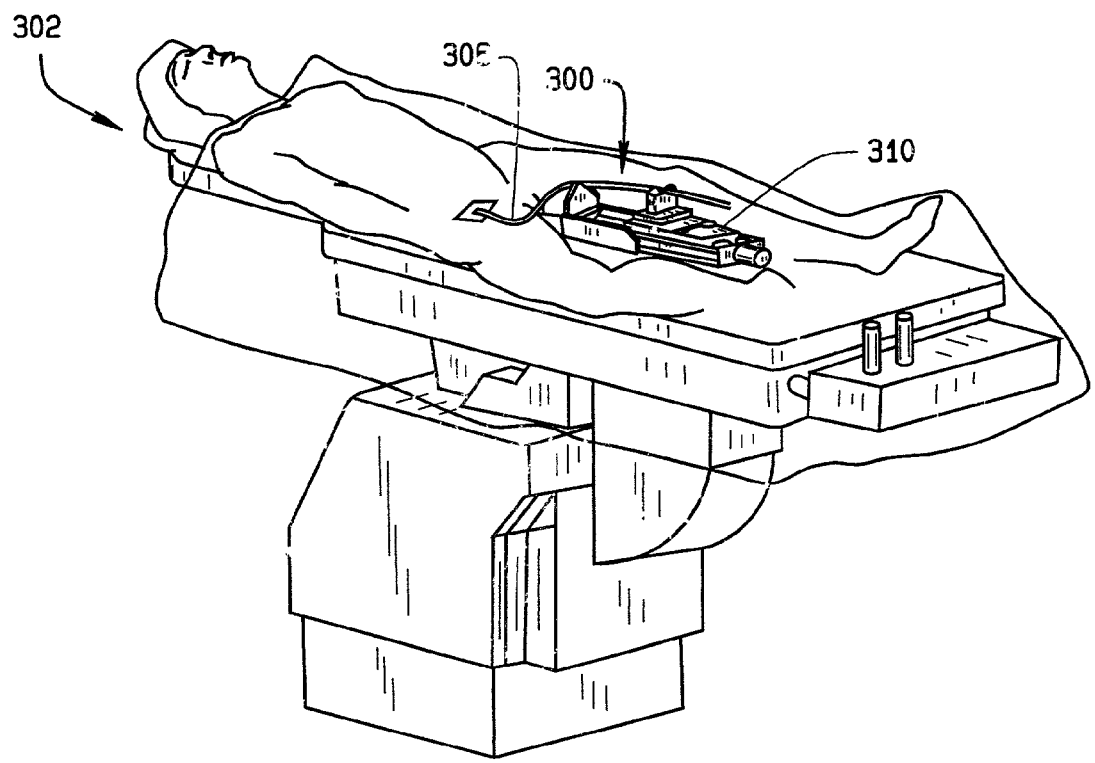
FIG. 9 is a perspective view of a patient on a bed, showing a drive unit of a second embodiment of an advancer system of the present invention.

A second embodiment of an advancer constructed according to the principles of this invention is indicated generally as 300 in FIG. 9. The advancer 300 comprises a drive unit 310, shown as it would be mounted on a patient table 302, for moving a medical device in a patient lying on the patient table. The medical device might be, for example, a catheter that is being advanced through a patient's vasculature, during a cardiac mapping procedure. The advancer 300 is adapted for moving a medical device through a sheath 306 and into a patient on the table 302. The advancer 300 also includes a control system having a controller or processor, and at least one operator input, for example, as previously described with respect to FIGS. 5 through 8.

Figure 10:
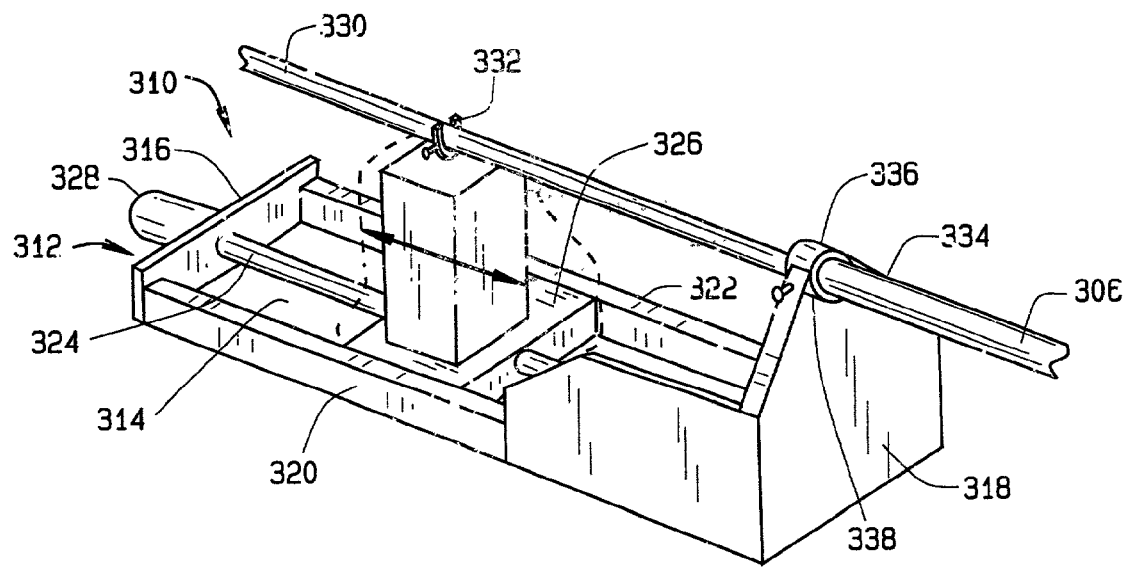
FIG. 10 is a perspective view of the drive unit shown in FIG. 9.

As shown in FIG. 10, the drive unit 310 comprises a frame 312 having a bottom 314, first and second ends 316 and 318, and first and second sides 320 and 322. A cover (not shown) may also be provided to enclose the drive unit 310. A lead screw 324 extends longitudinally through the frame 312, between the first and second ends 316 and 318. A carrier 326 is threadedly mounted on the lead screw 324. The lead screw 324 is driven by an electric motor 328 mounted on the first end 316 of the frame 312, such that rotation of the lead screw causes the carrier 326 to move within the frame 312. The drive unit 310 is placed on the table 302, e.g. between the legs of the patient. The drive unit 310 is sufficiently heavy to remain stationary if the patient moves or when the drive unit 310 is exposed to magnetic forces from a magnetic navigation system such as the MNS described in connection with FIGS. 5 and 6. The drive unit would preferably be made non-magnetic. The drive unit 310 rests on a sterile drape (not shown) and is placed in a sterile bag (not shown), and thus is reusable.

The motor 328 can be a stepper motor electrically connected to a controller such as the controller 100 (shown in FIGS. 5 and 6). In another embodiment the motor 328 is a servomotor. The drive unit 310 may include one or more limit switches (not shown) under control of the controller to prevent over-travel, as described above in relation to the drive unit 28 (shown in FIG. 2).

As shown in FIG. 10, a catheter 330 is attached to the carrier 326, via a U-shaped bracket 332 (or any other suitable means). The proximal end of the sheath 334, with a hemostasis valve 336 thereon, is secured on a fixture 338 on the second end 318 of the frame 312. Thus, as the carrier 326 moves in the frame 312, the catheter 330 moves relative to the sheath 306. The catheter 330 can be inserted into the bracket 332 at any point in its length. Thus, during a procedure, the catheter can be removed from the bracket, for example, for manual advancement, and reinserted at a different point along its length.

Figure 11:
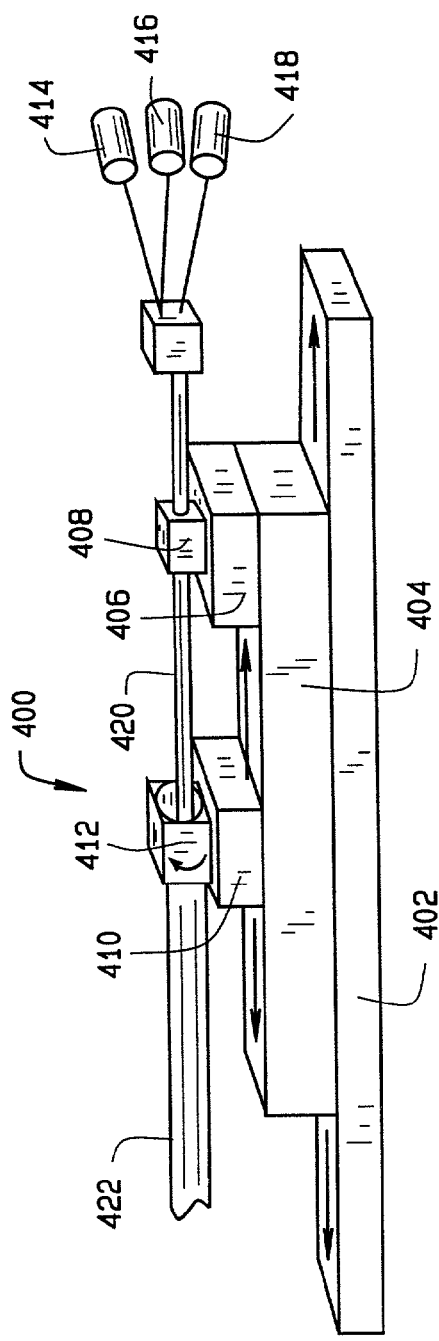
FIG. 11 is a perspective view of a drive unit of a third embodiment of an advancer system.
Figure 12:
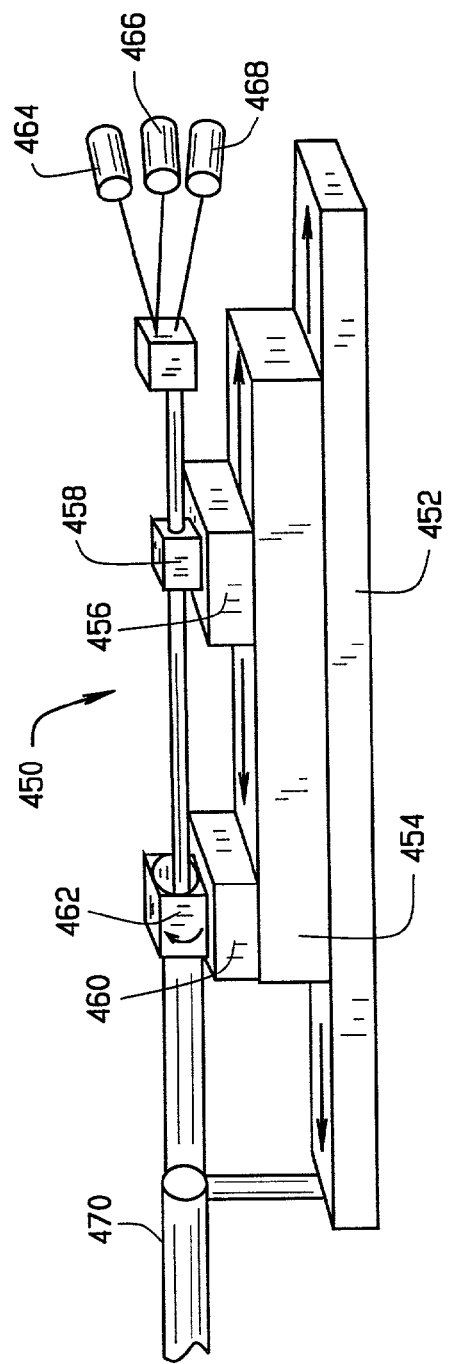
FIG. 12 is a perspective view of a drive unit of a fourth embodiment of an advancer system.

A third embodiment of an advancer drive unit is indicated generally as 400 in FIG. 11. The drive unit 400 comprises a base 402, on which a shuttle 404 is slideably mounted. A catheter mover 406 having a bracket 408 for engaging a catheter 420 is fixedly mounted on the shuttle 404. A sheath mover 410 having a bracket 412 for engaging a sheath 422 is slideably mounted on the shuttle 404. A first motor 414 moves the sheath mover 410 relative to the shuttle 404. A second motor 416 moves the shuffle 404 relative to the base 402. A third motor 418 causes the bracket 412 of the sheath mover to turn, causing the sheath 422 to turn to facilitate the advancement of the catheter 420. Thus, the catheter and sheath can be advanced and retracted together by movement of the shuttle 404 relative to the base 402, or the sheath can be advanced or retracted relative to the catheter by movement of the sheath mover 410 relative to the shuttle 404, or the catheter can be advanced or retracted relative to the sheath by a combination of movement of the shuttle 404 relative to the base 402, and the sheath mover 410 relative to the shuttle. In other embodiments, the catheter mover 406 and bracket 408 could be configured with a motor that causes the bracket 408, and catheter 420, to rotate. Thus either or both of the sheath and catheter could be rotated relative to a patient. A fourth embodiment of an advancer drive unit is indicated generally as 450 in FIG. 12. The drive unit 450 comprises a base 452, on which a shuttle 454 is slideably mounted. A catheter mover 456 having a bracket 458 for engaging the catheter is fixedly mounted on the shuttle 454. A sheath mover 460 having a bracket 462 for engaging the sheath is slideably mounted on the shuttle 454. A tube 470 for supporting the sheath is mounted to the base 452 and to a sheath insertion site on a patient. A first motor 464 moves the sheath mover 460 relative to the shuttle 454. A second motor 466 moves the shuttle 454 relative to the base 452. A third motor 468 causes the bracket 462 of the sheath mover to turn, causing the sheath to turn to facilitate the advancement of the catheter. Thus, the catheter and sheath can be advanced and retracted together by movement of the shuttle 454 relative to the base 452, or the sheath can be advanced or retracted relative to the catheter by movement of the sheath mover 460 relative to the shuttle 454, or the catheter can be advanced or retracted relative to the sheath by a combination of movement of the shuttle relative to the base, and the sheath mover relative to the shuttle.

Figure 13:
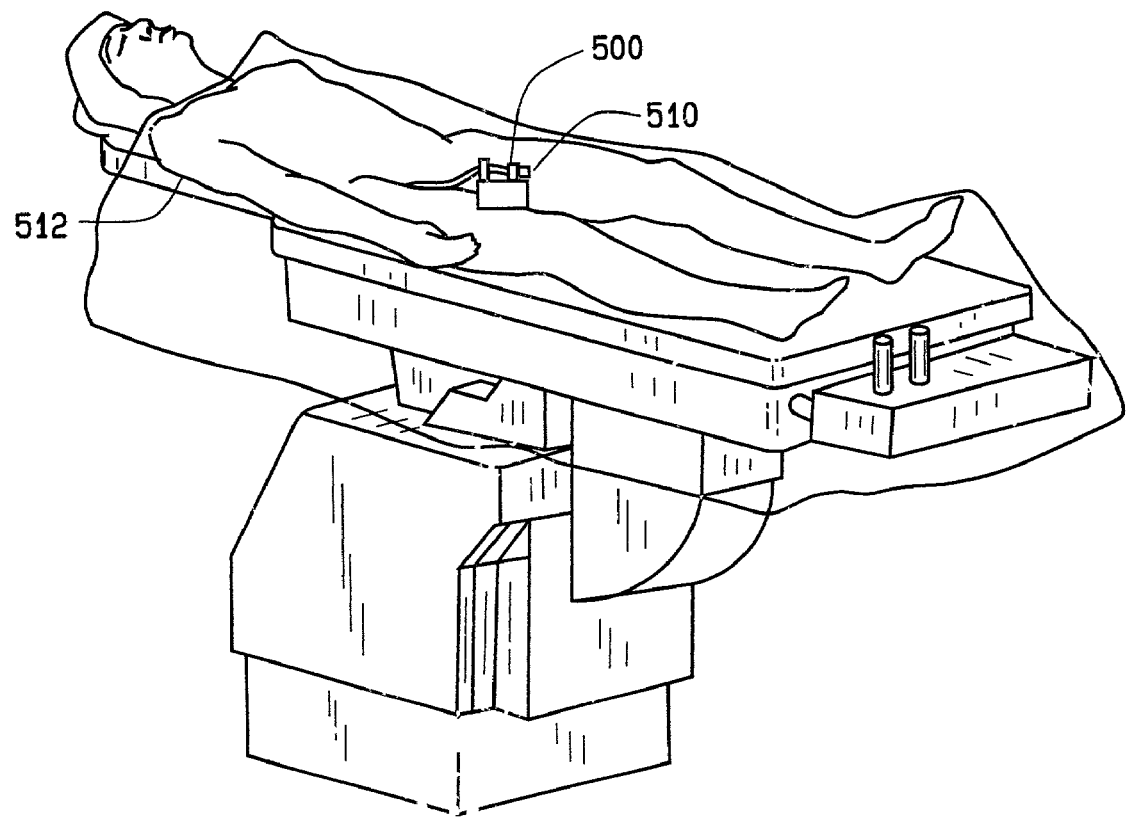
FIG. 13 is a perspective view of a drive unit of a fifth embodiment of an advancer system.
Figure 14:
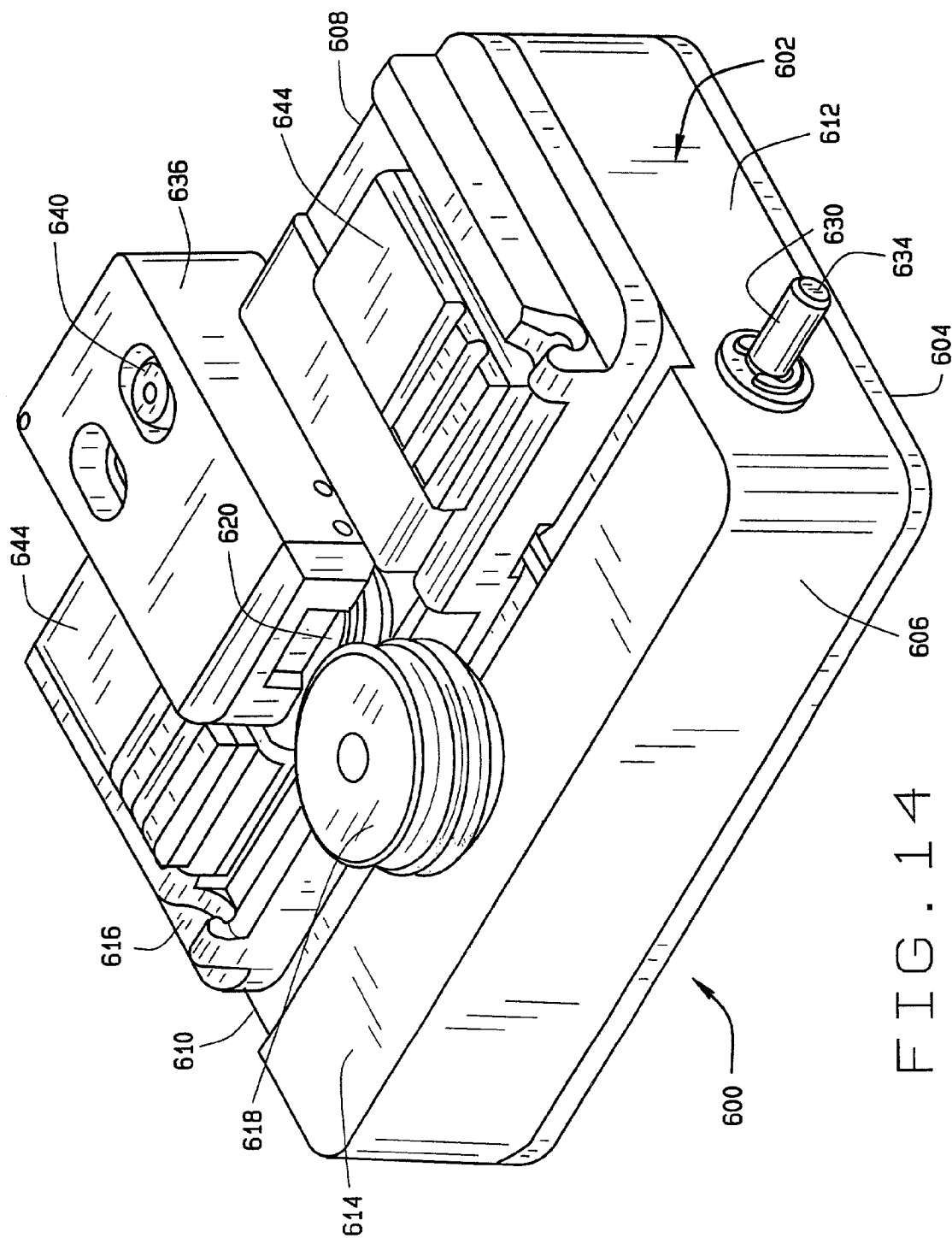
FIG. 14 is a perspective view of a sixth embodiment of an advancer system drive unit constructed according to the principles of this invention.
Figure 15:
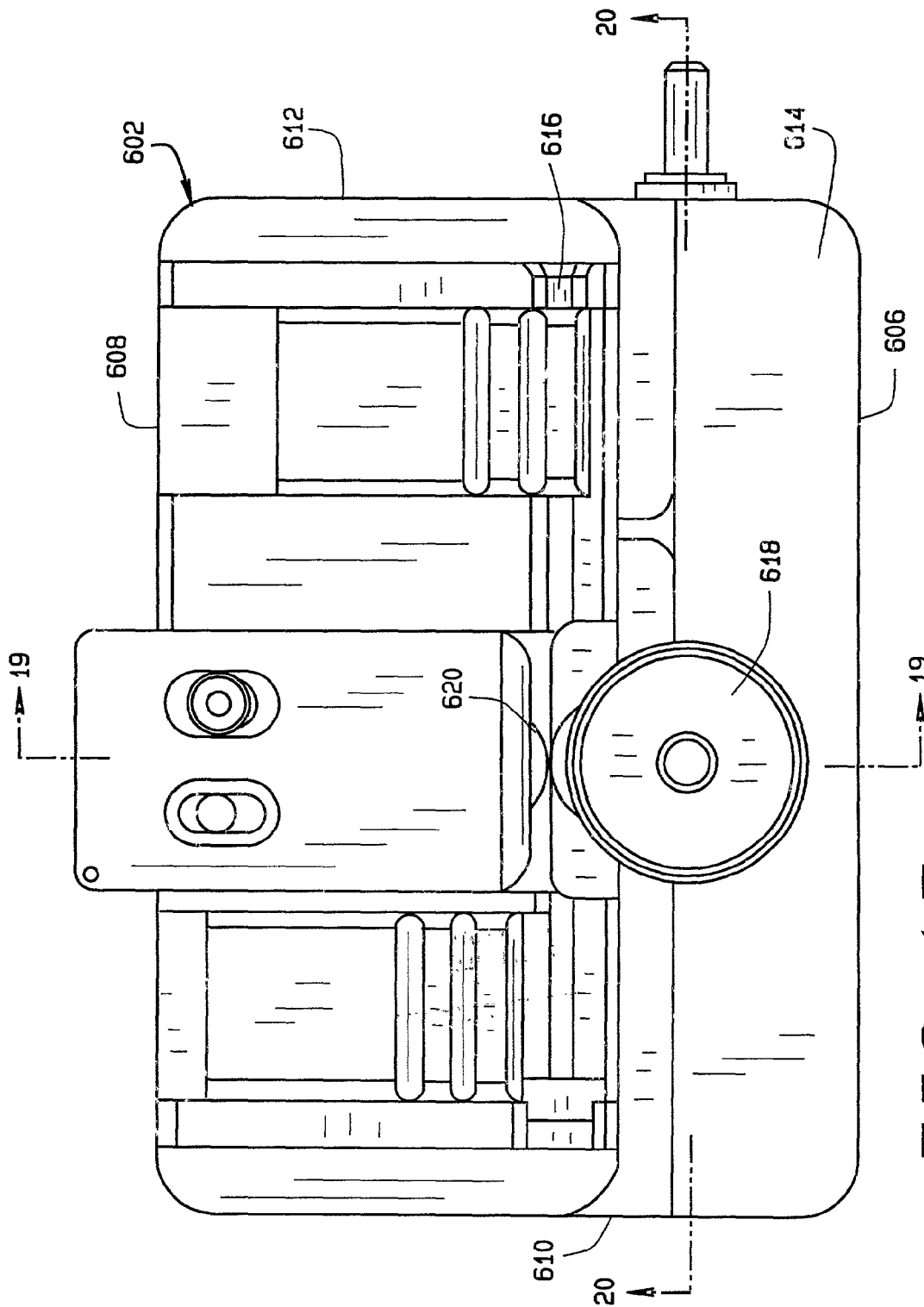
FIG. 15 is a top plan view of the drive unit of the sixth embodiment.
Figure 16:
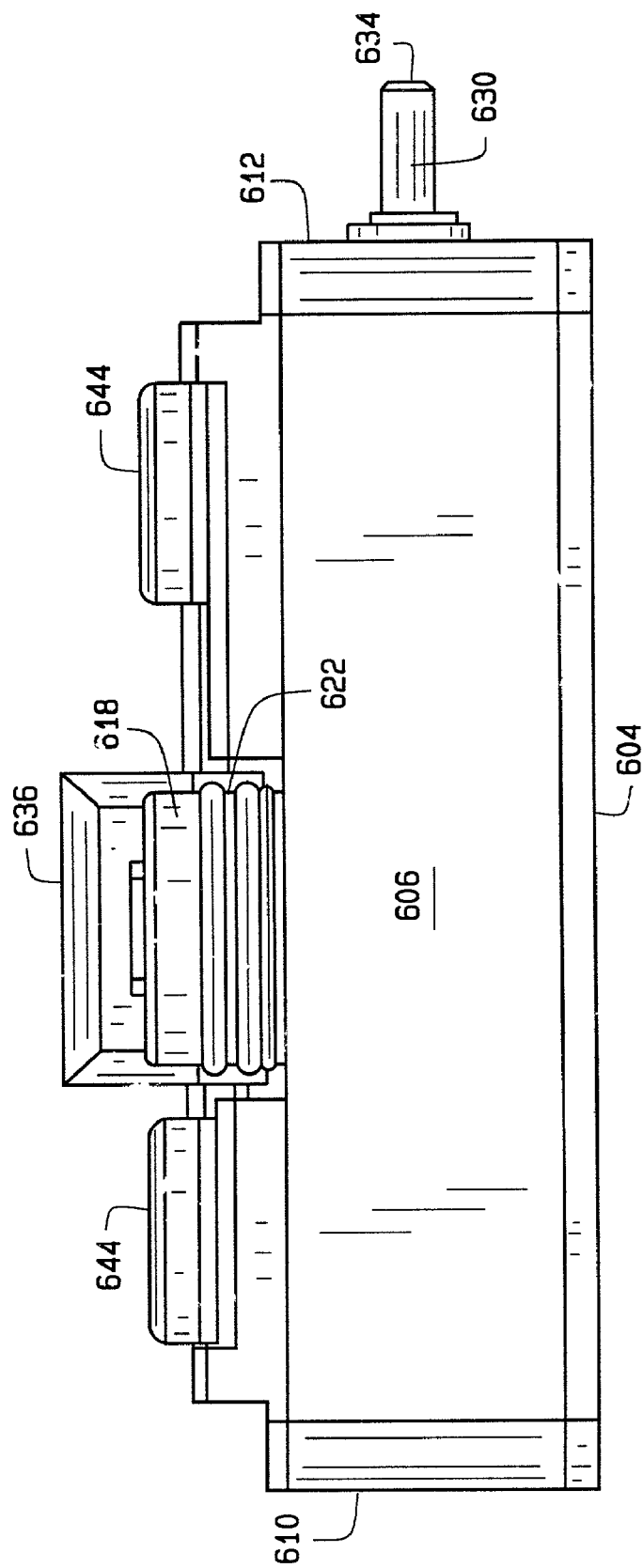
FIG. 16 is a front elevation view of the drive unit of the sixth embodiment.
Figure 17:
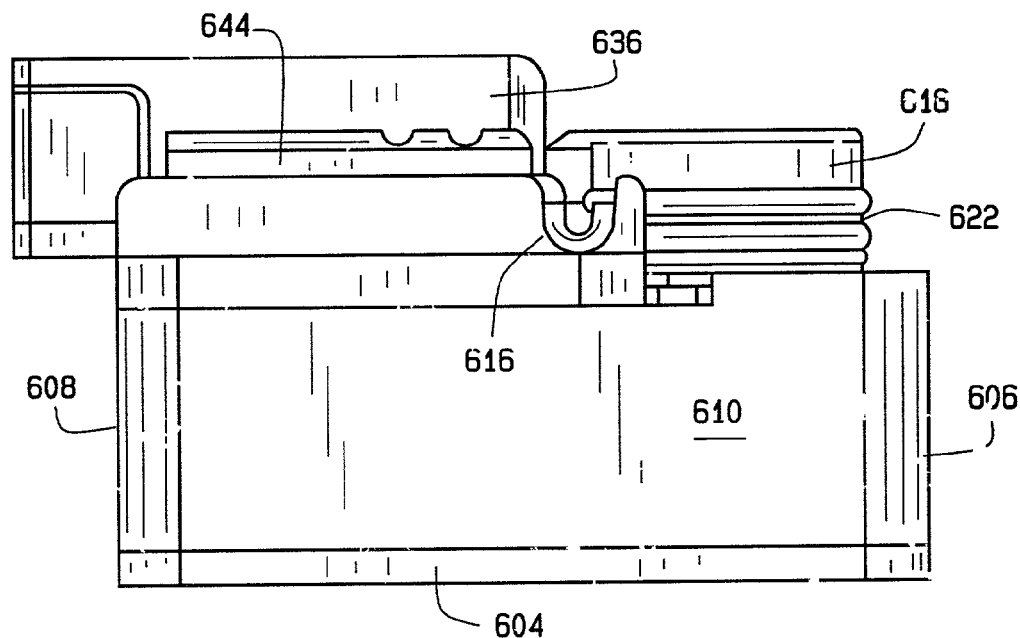
FIG. 17 is a left side elevation view of the drive unit of the sixth embodiment.
Figure 18:
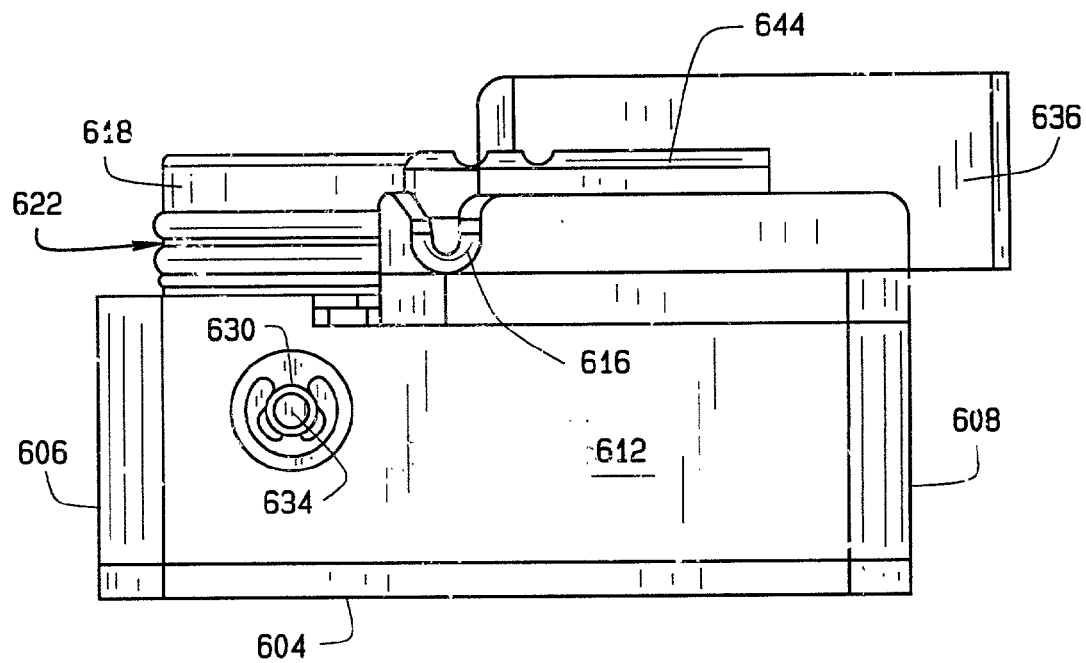
FIG. 18 is a right side elevation view of the drive unit of the sixth embodiment.
Figure 19:
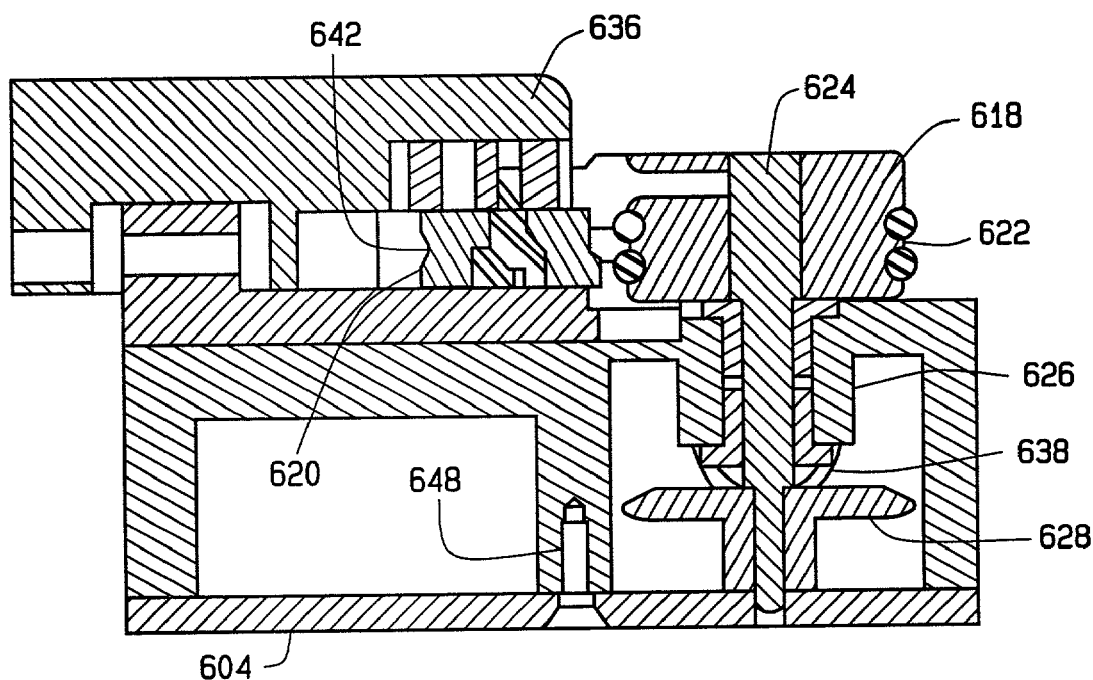
FIG. 19 is a cross-sectional view of the drive unit of the sixth embodiment, taken along the plane of line 19-19 in FIG. 15.

A fifth embodiment of an advancer drive unit constructed according to the principles of this invention is indicated generally as 500 in FIG. 13. The drive unit 500 includes a lightweight, e.g. less than one-pound, motor 510 and is attached, for example, on the thigh of a patient lying on a table 512. The motor 510 preferably is sterilizable and disposable, thus allowing a catheter and sheath to be directly attached to the advancer drive unit 500. The drive unit 500 is controlled by a control system (not shown in FIG. 13), as previously described in connection with FIGS. 5 through 8.

A sixth embodiment of an advancer drive unit is indicated generally as 600 in FIGS. 14 through 20. The drive unit 600 comprises a generally hollow box-shaped housing 602 having a bottom 604, a front 606, a back 608, left and right sides 610 and 612, and a top 614. A slot 616 extends transversely across the top 614. Opposed wheels 618 and 620 protrude into the slot 616 to engage an elongate medical device, such as a catheter. In this embodiment the wheel 618 is a driven wheel, and the wheel 620 is an idler wheel.

The wheel 618 has two circumferentially extending rings on its surface, forming a circumferentially extending groove 622 between them for engaging an elongate medical device. The wheel 618 is mounted on a shaft 624, which is journaled in a vertically extending passage 626. A bevel gear 628 is mounted on the shaft 624. A drive shaft 630, having first and second ends 632 and 634, is journaled in a horizontally extending passage 646. The first end 632 of the drive shaft 630 has a bevel gear 638 that engages the bevel gear 628 on the shaft 624. The second end 634 of the drive shaft 630 extends out the side 612 of the housing 604 and is connected to a drive motor (not shown). The wheel 620 is mounted underneath a removable support 636 on the top 614 of the housing 602. A screw 648 rotatably mounts the wheel 620 to and underneath the support 636. Screws 640 secure the support 636 on the top 614 of the housing. The surface of the wheel 620 is preferably contoured, with a recess 642 aligned with the groove 622 on the wheel 618 to firmly engage an elongate medical device between them.

There are two sliding covers 644 on either side of the opposed wheels 618 and 620, that can be slid to selectively extend over the slot 616 in the top 614, to help retain the elongate medical device in the slot.

In use the advancer drive unit 600 is connected to a controlled motor, such as a stepper motor. An elongate medical device is loaded into the drive unit by laying and pressing a length of the device into the slot 616 in the top 614 of the housing 602, and between the opposed wheels 618 and 620, until the device is engaged by the wheels between the groove 622 and the recess 642. When the motor is driven, the drive shaft 630 turns, turning bevel gear 634, which in turn turns bevel gear 628, turning shaft 624, and thus wheel 618, advancing or retracting the elongate medical device.

Figure 21:
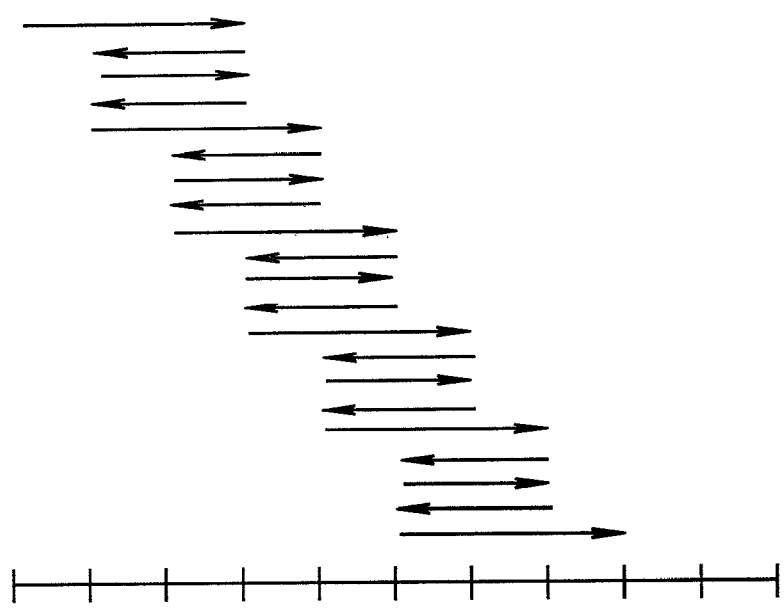
FIG. 21 is a diagram illustrating a method of advancing and retracting a catheter to reduce effects of static friction on the motion of a catheter, achievable with the methods and apparatus of the present invention.
Figure 20:
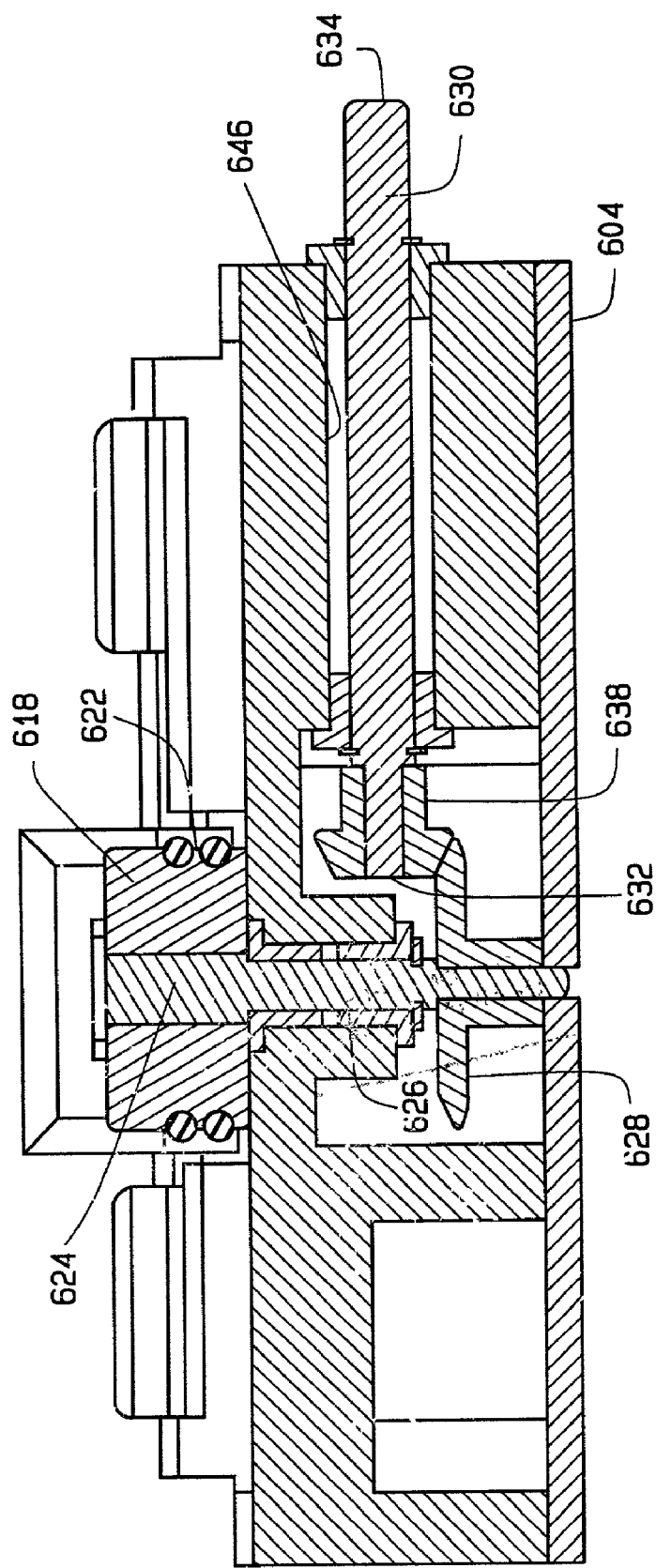
FIG. 20 is a cross-sectional view of the drive unit of the sixth embodiment, taken along the plane of line 20-20 in FIG. 15.

When an elongate medical device is being advanced in a body, friction between the device and the tissues of the body may cause difficulty in advancing the device. The inventors have discovered that by keeping the medical device in motion, static friction can be eliminated. Thus upon advancing a medical device, the inventors have found it more advantageous to advance the medical device and withdraw it slightly, rather than simply advance the medical device. More preferably, as shown in FIG. 21, the device would be advanced a first distance, e.g. 0.003 inches, then retracted a second distance, e.g. 0.002 inches, advanced the second distance, e.g. 0.002 inches, and retracted the second distance 0.002 inches. Then the cycle is repeated, the device advancing a net 0.001 inches with each cycle. When an embodiment of the present advancer system is idling, the advancer drive unit may also be operated to successively move the medical device forward and back or to "stutter" to reduce static friction. Alternatively, immediately before the medical device is advanced, the advancer can be controlled to begin advancing and retracting the device to reduce static friction.

Figure 26:
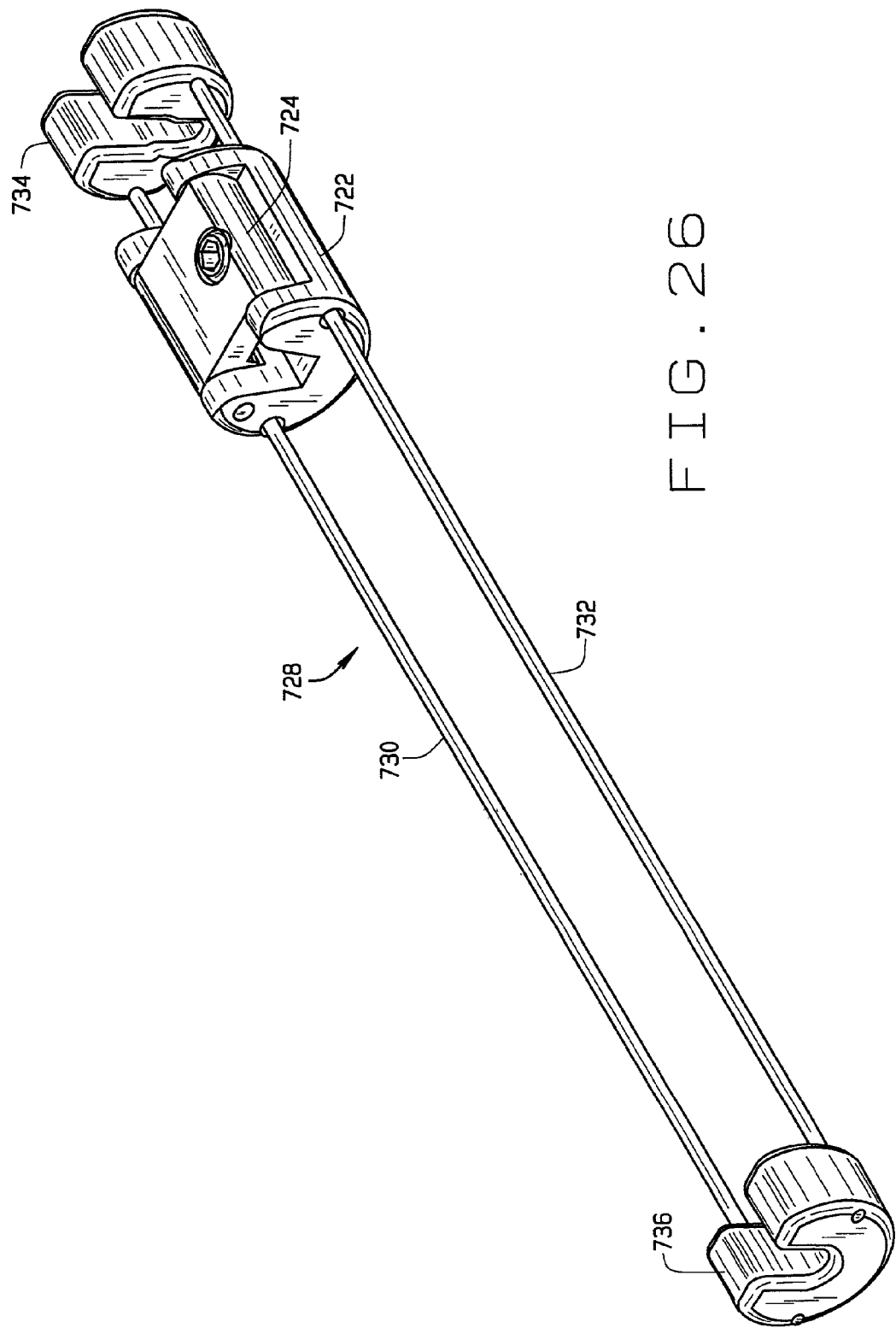
FIG. 26 is a perspective view of a sliding support used in the slide unit shown in FIG. 22.
Figure 27:
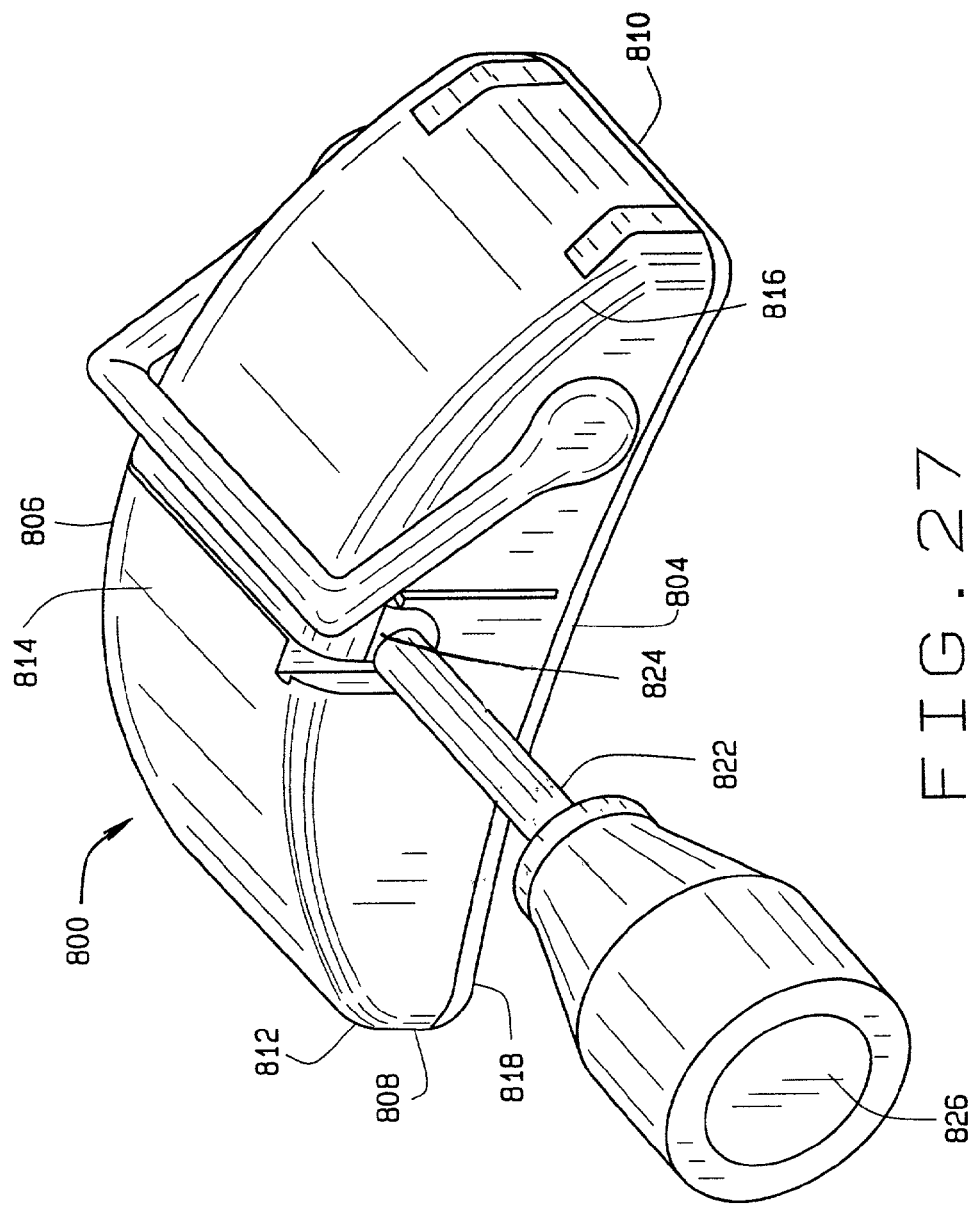
FIG. 27 is a frontal perspective view of a drive unit constructed according to an eighth embodiment of the present invention.
Figure 28:
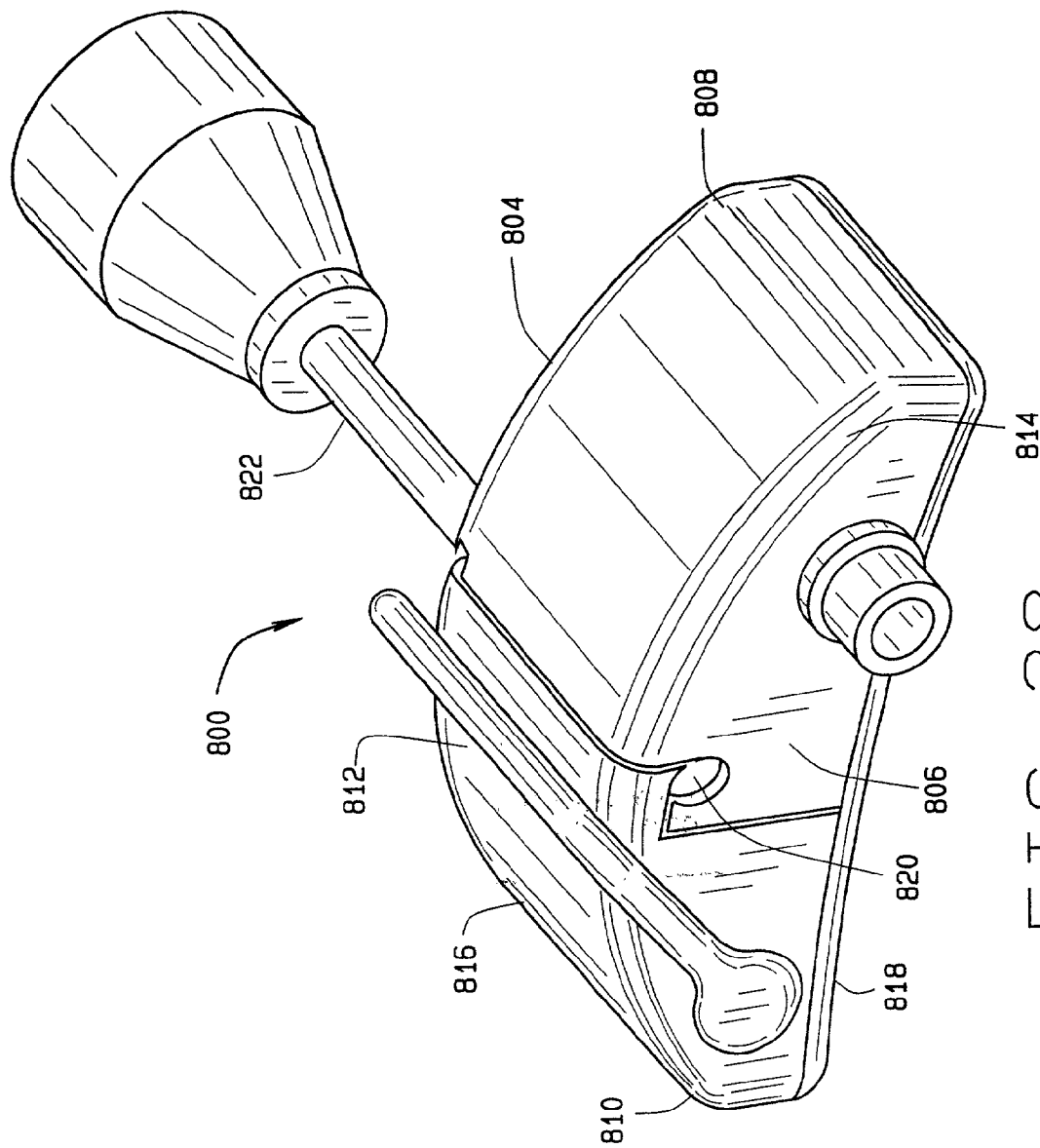
FIG. 28 is a rear perspective view of the drive unit shown in FIG. 27.
Figure 29:
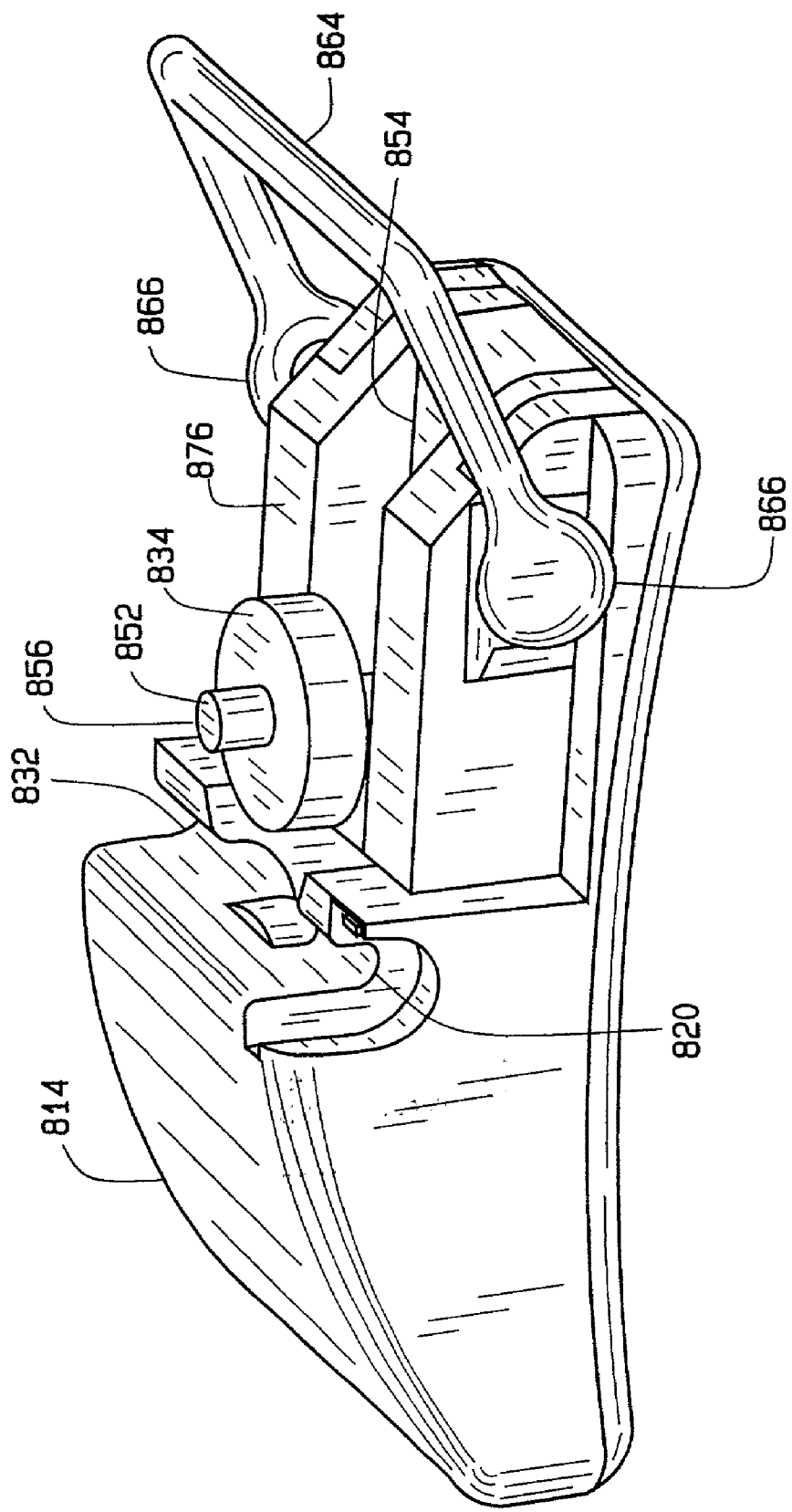
FIG. 29 is a frontal perspective view of the drive unit shown in FIG. 27, with the sliding cover removed.

A seventh embodiment of a slide unit is indicated generally as 700 in FIGS. 22 and 23. Portions of the slide unit 700 are shown in FIGS. 24 through 26. The slide unit 700 is adapted to be connected to a drive unit, such the drive unit 28 (shown in FIG. 2). The slide unit 700 comprises an elongate housing 702, formed in left and right halves 704 and 706 that are mounted on a bottom plate 708. The housing 702 comprises a proximal end 710 and a distal end 712. The bottom 708 has dovetail cutouts 714 which receive dovetail projections 716 on the bottoms of the left and right halves 704 and 706. There is a channel 720 in the housing 702, in which a slide 722 can reciprocate. The slide 722 has a latch 724 that can engage an elongate medical device such as a catheter. The slide 722 also engages a wire 726, for example, from a control cable connected to the drive unit 28, described above. Thus, movement of the wire 726 causes the slide 722 to move in the channel 720 in the housing 702. A slidable support 728 is also positioned in the channel 720. The slidable support comprises two rods 730 and 732 with a proximal support 734 and a distal support 736. The proximal and distal supports 734 and 736 engage and support an elongate medical device extending through the slide unit 700. The slide 722 is advanced within the channel 720 until it engages the distal support 736, and then the slide 722 and the distal support advance together. Similarly, the slide 722 retracts until in engages the proximal support 734, and the slide and the proximal support retract together. The slide unit 700 has an attachment 740 for a sheath at the distal end 712 of the housing 702. There an attachment at the proximal end 710 for the outer sheath 62 of the control cable.

In operation, the advancer 700 is opened by sliding the right half 706 away from the left half, and an elongate medical device such as a catheter is installed therein. The catheter is installed in the slide 722, and the latch 724 closed to secure the catheter. The catheter is engaged in the supports 734 and 736, and the two halves of the housing are slid together. Thereafter, the drive unit 28 is used to move the wire 726, and thereby move the slider 722, which causes the catheter to move inwardly and outwardly.

An eighth embodiment of a drive unit constructed according to the principle of this invention is indicated generally as 800 in FIGS. 27 through 33. The drive unit 800 preferably is small 2.6 inches long, 1.1 inches wide (the longitudinal direction), and 1 inch high sterile and disposable. It can be used close to an insertion site on a patient. The drive unit 800 generally is preferably fabricated of non-magnetic materials, and more preferably of non-metallic materials, or at least substantially of non-magnetic materials. The exterior is made from ABS or other suitable material, and the interior components are Delrin or other suitable polymer. The drive unit is at least primarily non-magnetic i.e. it is sufficiently non-magnetic that it will not interfere with the operation of a magnetic surgery system that applies fields of 0.5 T or more to the operating region to orient the distal tip of the elongate medical device, and that it will not interfere with the operation of a magnetic localization system for magnetically localizing the position of the distal end of the elongate medical device in the operating region. The drive unit is preferably also at least primarily non-metallic i.e. it is sufficiently non-metallic that it will not interfere with the operation of a magnetic localization system for magnetically localizing the position of the distal end of the elongate medical device in the operating region. Preferably, the device is sufficiently non-magnetic and non-metallic that it can be left in place during MR imaging.

The drive unit 800 comprises a front 804, a back 806, a right side 808 and a left side 810. A generally hollow curved housing 812 comprises a base 814 and a sliding cover 816 resting on a bottom 818. The base 814 is affixed to the bottom 818 by a pair of opposed pins (not shown) through aligned holes 802 in the base and bottom. The pins are preferably a non-magnetic, non-corrosive material such as stainless steel. The sliding cover 816 is movably attached to the bottom 818 by a pair of opposed pins (not shown) through a pair of holes 828 in the cover (shown in FIG. 30) and a pair of horizontal slots 872 in the bottom 818 (shown in FIG. 31). Thus the cover 816 can be slid horizontally away from and toward the base 814 as limited by the slots 872, as further described below.

A slot 820 in the base 814 extends longitudinally through the drive unit 800 and is configured to hold an elongate medical device such as a catheter. A hemostasis valve adapter 822 is mounted in a front end 824 of the slot 820. The catheter can be extended through the adapter 822 into an attached sheath or introducer (not shown in FIGS. 27 through 33) having a distal end inserted in a patient. The adapter 822 preferably is flexible and has an interior surface 826 of Teflon® or other material having a coefficient of friction sufficiently low to aid in preventing buckling of the catheter as it moves through the drive unit 800. The slot 820 is covered by the sliding cover 816 when the cover 816 is closed as further described below.

Opposed wheels 832 and 834 protrude into the slot 820 to engage the catheter. In this preferred embodiment, wheel 832 is a driven wheel, and wheel 834 is an idler wheel. The wheels 832 and 834 may be fabricated in various ways depending, for example, on the type, material and/or flexibility of the medical device to be driven through the drive unit. Thus the wheels may be fabricated of a hard material that can flow in an injection mold sufficiently to form small teeth 836 that can grip a catheter as it is driven past the wheels. "Small" teeth include, for example, teeth having a height of 0.01 inch. Alternatively, the wheels 832 and 834 can be fabricated of a soft material, for example, rubber, such that the wheels would contour and deform slightly so as not to crush a catheter being driven by the wheels. In yet another embodiment, one or both of the wheels 832 and 834 can be circumferentially grooved, like the wheel 618 of the drive unit 600 (shown in FIGS. 14 through 20), for engaging an elongate medical device.

The driven wheel 832 is mounted on a shaft 838. The shaft 838 is mounted vertically in and between a base socket 840 (shown in FIG. 33) and a bottom socket 842 (shown in FIG. 31). A worm gear 844 is mounted on the shaft 838. A rigid drive shaft 848 is rotatably mounted longitudinally in the base 814 and extends through the back 806 of the drive unit 800. The drive shaft 848 has a worm 850 that engages the worm gear 844 on the shaft 838.

A flexible drive shaft 846 is connected to the rigid drive shaft 848 via a connector 884, and to a drive motor 886 via a connector 888. The drive motor 886 is a bi-directional controlled motor, for example, a stepper motor, that preferably can be controlled remotely as previously described in connection with the drive unit 28 (shown in FIGS. 1 through 5). In other embodiments, the motor 886 can be a servomotor. The flexible drive shaft 846 includes a 3/16-inch-diameter flexible coil 890, preferably fabricated of non-magnetic stainless steel and covered by a flexible clear plastic tubing 892. The coil 890 is rotatable by the motor 886 in forward and reverse directions to provide bidirectional movement of the drive wheel 832. The flexible drive shaft 846 preferably is sterile for use within a sterile operating area. The drive shaft 846 also preferably is sufficiently long (for example, approximately four feet long) to allow it to be driven by the motor 886 while the motor remains outside the sterile area. In other embodiments, the motor 886 is also sterile, is used within the sterile operating area, and is disposed of after completion of the operating procedure.

The idler wheel 834 is mounted on a shaft 852 snap-fitted into and extending vertically from a slot (not shown) in a floor 854 of the base 814. An upper end 856 of the shaft 852 fits in a groove 858 (shown in FIG. 32) extending transversely along an inner surface 860 of the sliding cover 816. A spring 880 is stretched, beneath the base floor 854, between an edge 882 of the sliding cover 816 and a vertical support 894 of the base 814. The spring is a non-magnetic, non-corrosive material such as stainless steel. The spring force thus pulls the sliding cover 816 horizontally toward the idler wheel shaft 852. When the cover 816 is in a closed position, the force of the spring 880 causes an end 896 of the groove 858 to press against the shaft upper end 856. The idler wheel 834 thus is pressed against a medical device engaged between the wheel 834 and the driver wheel 832.

Figure 30:
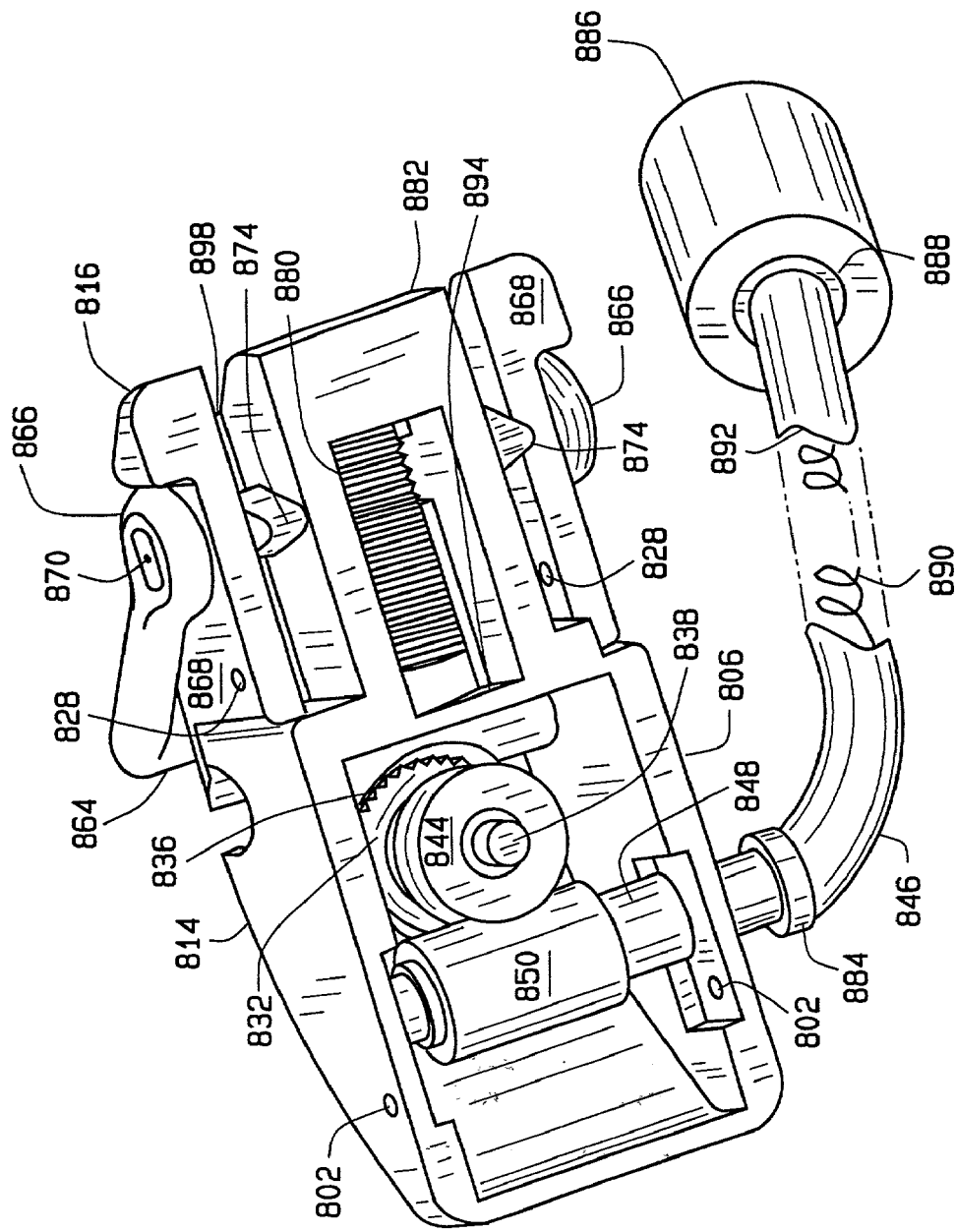
FIG. 30 is a bottom perspective view of the drive unit shown in FIG. 27, with the bottom removed.
Figure 31:
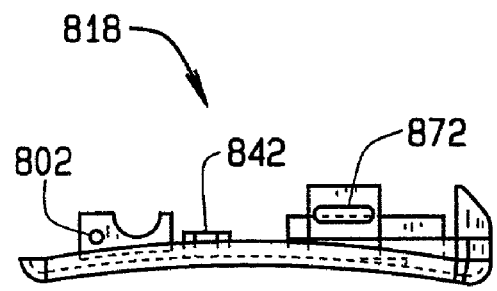
FIG. 31 is a side elevation sectional view of the bottom of the drive unit shown in FIG. 27.
Figure 32:
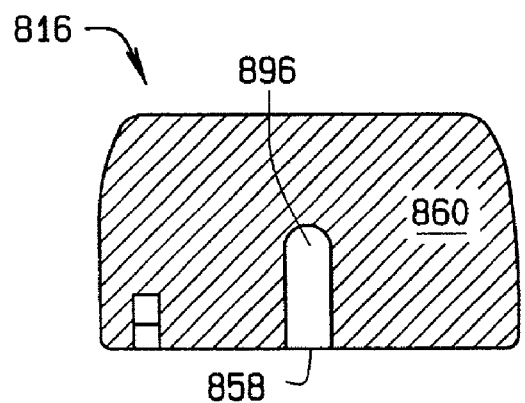
FIG. 32 is a plan sectional view of the inside of the sliding cover of the drive unit shown in FIG. 27.
Figure 33:
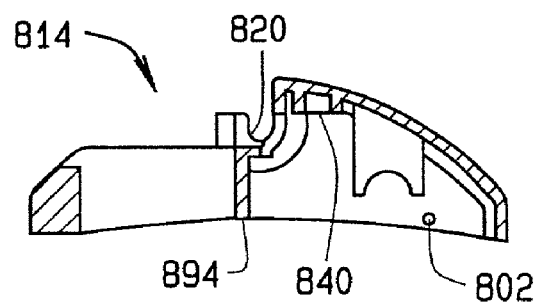
FIG. 33 is a side elevation sectional view of the base of the drive unit shown in FIG. 27.

A generally U-shaped lever arm or handle 864 is used to open the sliding cover 816 relative to the base 814. Two ends 866 of the handle are rotatably mounted over two sides 868 of the sliding cover 816 on a pair of opposed pivots 870. The pivots 870 further extend toward each other through two cams 874. Although not attached to the base 814, each of the cams is limited in its range of motion by an upper shelf 898 in the base 814. The cover 816 is biased by the spring 880 in a closed position against the shaft upper end 856, the cams are biased in an upright position as shown in FIG. 30, and the handle 864 is biased to lie flush against the cover 816.

To insert an elongate medical device into the drive unit 800, a user rotates the handle 864 away from the slot 820 in the base 814. As the handle 864 rotates on the pivots 870, the cams 874 also rotate to lie flat against the bottom 818. The pins through the holes 828 and bottom slots 872 move horizontally in the slots 872 away from the slot 820 in the base 814. The sliding cover 816 thus is opened sufficiently to uncover the slot 820 in the base 814. The groove 858 in the underside of the cover 816 allows the cover 816 to be slid open, and subsequently closed, without disturbing the upper end 856 of the idle wheel shaft 852. The cams 874 are positioned so as to lock the cover 816 in the open position. An elongate medical device is loaded into the drive unit 800 by laying and pressing a length of the device into the slot 820 between the opposed wheels 832 and 834, until the device is engaged by the wheels, for example, between two grooves in wheels 832 and 834 as previously described. The user then presses the handle 864 toward the slot 820, thereby causing the cams to return to the upright position. The sliding cover is pulled by the spring 880 into a closed position over the elongate medical device. When the motor is driven, the rigid drive shaft 848 turns, turning the worm 850, which in turn drives the worm gear 844, turning the drive wheel shaft 838 and thus the drive wheel 832. The medical device is advanced and/or retracted through the adapter 822 and attached sheath.

Figure 34:
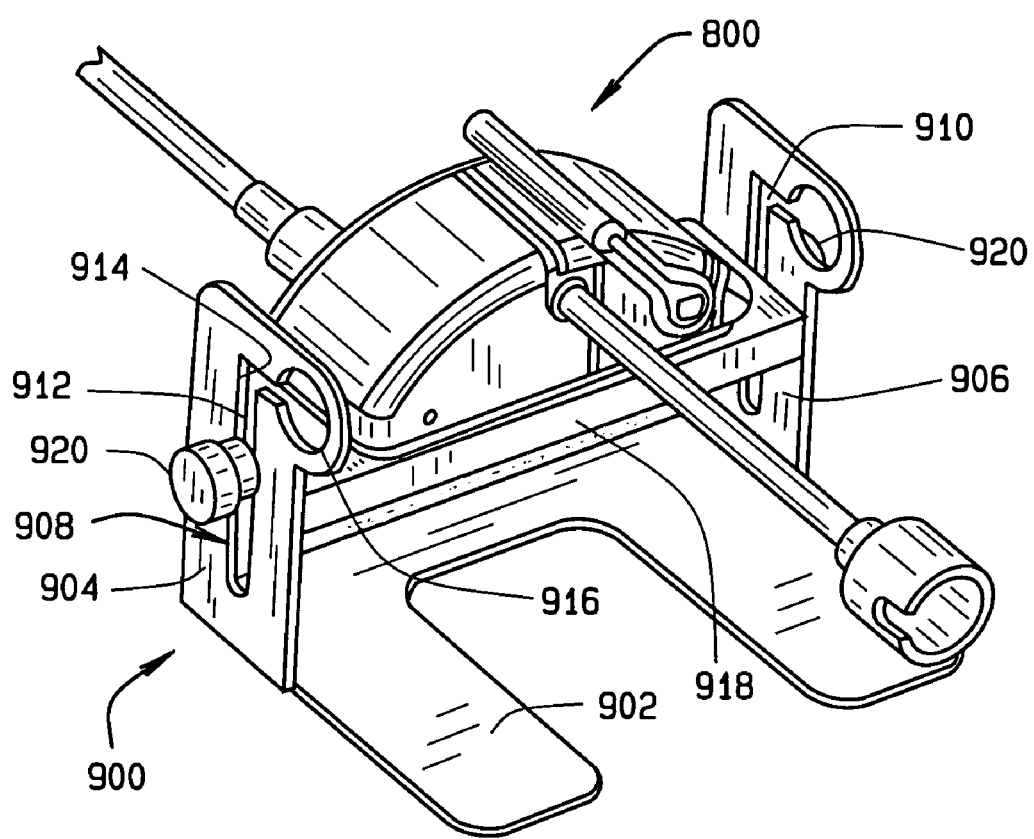
FIG. 34 is a perspective view of the drive unit of the eighth preferred embodiment, shown in a mounting bracket.

The drive unit 800 is shown in FIG. 34, as it would be mounted on a support bracket 900. The support bracket 900 comprises a flexible, generally U-shaped base 902, having a bottom surface adapted to be secured on the patient. The bottom surface may be provided with a double stick adhesive, with a protective sheet, so that the support bracket 900 can be attached to patient, typically on the patients thigh, adjacent the femoral artery. There are opposed vertical struts 904 and 906 on either side of the U-shaped base 902. The struts have slots 908 and 910, therein. The slots 908 and 910 are mirror images of one another, comprising a vertically extending portion 912, a horizontally extending portion 914, and a circular portion 916. A bed 918 is mounted between the struts 904 and 906, with thumb screws 920 extending through the slot and into the bed. Each thumb screw can be tightened to engage the margins of the strut surrounding the slot to fix the end of the bed. The drive unit 800 can be secured to the bed, for example with double-stick adhesive provided on the surface of the bed, and covered with a removable protective sheet. The support bracket allows the drive unit 800 to be oriented at various angles to accommodate the catheter orientation at the entry point to the body, (typically at the femoral artery).

The above described drive units can be varied in their drive characteristics. For example, rotary drive units 600 and 800 can provide a driving force to a medical device while preventing slippage of the device during advancement or retraction. A drive unit utilizing a slider, e.g. the drive unit 28 in combination with slider 30 or 700, tends to apply less pressure against a device than would a rotary drive unit. Thus, in one embodiment, two drive units could be controlled together by an advancer control system and/or magnetic navigation system to move one elongate device relative to another elongate device in a patient. For example, a catheter could be advanced and retracted using a rotary drive unit, while a sheath holding the catheter could be advanced and retracted using a drive unit/control cable/slider combination. Other embodiments of course are possible, in which drive units, control cables and/or sliders are utilized and/or combined to advance and/or retract on or more elongate medical devices.

The above-described embodiments of an advancer system provide a wide variety of options for configuring such a system. A drive unit, for example, may be selected for attachment to a patient table or to a body part of the patient. For procedures in which magnets are used to move and/or steer an elongate device in a patient, a non-magnetic drive unit can be used within the operating site without causing magnetic interference. Where joystick devices are provided at the patient table and in a control room, an operating physician can use the system at the patient table during procedure setup and then can perform the procedure from the control room outside an imaging x-ray field. Thus the physician can avoid repeated x-ray exposures.

Other changes and modifications may be made to the above-described embodiments without departing from the scope of the present invention, as recognized by those skilled in the art. Thus the invention is to be limited only by the scope of the following claims and their equivalents.

What is claimed is:

1. A method of moving an elongate medical device having proximal and distal ends, the method comprising laying and pressing a portion of the elongate medical device between the proximal and distal ends between an opposed pair of wheels on opposite sides of a slot in the base of an advancer, moving a cover to at least partially close the slot to retain the device in the slot, and turning at least one of the wheels to move the device; wherein moving the cover causes at least one of the wheels to protrude into the slot.

2. The method of claim 1 wherein the step of moving the cover includes moving at least one of the pair of opposed wheels to bring the wheels closer together to engage an elongate medical device between them.

\* \* \* \* \*